United States Patent
Sugai et al.

(10) Patent No.: US 9,376,371 B2
(45) Date of Patent: Jun. 28, 2016

(54) TRIPHENYLAMINE DERIVATIVE, METHOD FOR MANUFACTURING THE SAME, AND ELECTROPHOTOGRAPHIC PHOTOSENSITIVE MEMBER

(71) Applicant: KYOCERA DOCUMENT SOLUTIONS INC., Osaka (JP)

(72) Inventors: Fumio Sugai, Osaka (JP); Kensuke Kojima, Osaka (JP); Kenji Kitaguchi, Osaka (JP); Hideki Okada, Osaka (JP)

(73) Assignee: KYOCERA Document Solutions Inc., Osaka (JP)

( * ) Notice: Subject to any disclaimer, the term of this patent is extended or adjusted under 35 U.S.C. 154(b) by 0 days.

(21) Appl. No.: 14/288,542

(22) Filed: May 28, 2014

(65) Prior Publication Data

US 2014/0357895 A1    Dec. 4, 2014

(30) Foreign Application Priority Data

May 31, 2013  (JP) ................................. 2013-116126

(51) Int. Cl.

| C07C 217/92 | (2006.01) |
| C07C 209/10 | (2006.01) |
| G03G 5/06   | (2006.01) |
| C07C 211/54 | (2006.01) |

(52) U.S. Cl.
CPC .............. *C07C 217/92* (2013.01); *C07C 209/10* (2013.01); *C07C 211/54* (2013.01); *G03G 5/0614* (2013.01); *G03G 5/0618* (2013.01); *G03G 5/0672* (2013.01)

(58) Field of Classification Search
CPC .................................................... C07C 217/92
See application file for complete search history.

(56) References Cited

FOREIGN PATENT DOCUMENTS

| JP | 2005-289877 A | 10/2005 | |
| JP | 2008024656 | * 7/2006 | ............ C07C 211/64 |
| JP | 2010-070464 A | 4/2010 | |

* cited by examiner

*Primary Examiner* — Clinton Brooks
(74) *Attorney, Agent, or Firm* — Studebaker & Brackett PC

(57) ABSTRACT

A triphenylamine derivative is represented by General Formula (1).

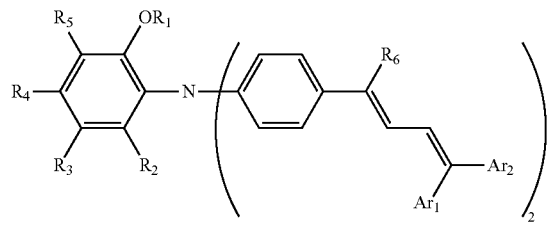

(1)

In General Formula (1), $OR_1$ represents an alkoxy group having 2 to 8 carbon atoms. $R_2$ to $R_6$ each independently represent a hydrogen atom or an alkyl group having 1 to 8 carbon atoms. $Ar_1$ and $Ar_2$ each independently represent a hydrogen atom, an aryl group having 6 to 20 carbon atoms and optionally substituted with an alkyl group having 1 to 6 carbon atoms, an aryl group having 6 to 20 carbon atoms and optionally substituted with an alkoxy group having 1 to 6 carbon atoms, a cycloalkyl group having 3 to 10 carbon atoms, or a 3- to 10-membered heterocyclic group. Note that the case where $Ar_1$ and $Ar_2$ are both a hydrogen atom is excluded.

9 Claims, 3 Drawing Sheets

TRIPHENYLAMINE DERIVATIVE, METHOD FOR MANUFACTURING THE SAME, AND ELECTROPHOTOGRAPHIC PHOTOSENSITIVE MEMBER

INCORPORATION BY REFERENCE

The present application claims priority under 35 U.S.C. §119 to Japanese Patent Application No. 2013-116126, filed May 31, 2013. The contents of this application are incorporated herein by reference in their entirety.

BACKGROUND

The present disclosure relates to a triphenylamine derivative, a method for manufacturing the same, and an electrophotographic photosensitive member.

Electrophotographic printers and multifunction peripherals include an electrophotographic photosensitive member as an image bearing member. Typically, the electrophotographic photosensitive member includes a conductive substrate and a photosensitive layer. The photosensitive layer is disposed directly or indirectly on the conductive substrate. The photosensitive layer contains a charge generating material, a charge transport material, and a resin. The resin binds the charge transport material and the charge generating material. Such photosensitive members that include a photosensitive layer containing an organic material, such as a resin, are called electrophotographic organic photosensitive members.

When an electrophotographic organic photosensitive member includes a charge transport layer having a charge transport function and a charge generating layer having a charge generating function that are formed as two separate layers, such an electrophotographic organic photosensitive member is called a multi-layer electrophotographic photosensitive member. On the other hand, when an electrophotographic organic photosensitive member contains both a charge transport material and a charge generating material in one and the same photosensitive layer (when a single photosensitive layer is included), such an electrophotographic organic photosensitive member is called a single-layer electrophotographic photosensitive member.

Photosensitive members also include electrophotographic inorganic photosensitive members containing an inorganic material (such as selenium photosensitive members, and amorphous silicon photosensitive members).

As compared with electrophotographic inorganic photosensitive members, electrophotographic organic photosensitive members have little effect on the environment and are readily formed into a film and easy to manufacture. Therefore, electrophotographic organic photosensitive members are currently used in many image forming apparatuses.

The charge transport materials usable in single- and multi-layer electrophotographic organic photosensitive members include triphenylamine derivatives.

SUMMARY

A triphenylamine derivative according to the present disclosure is represented by General Formula (1).

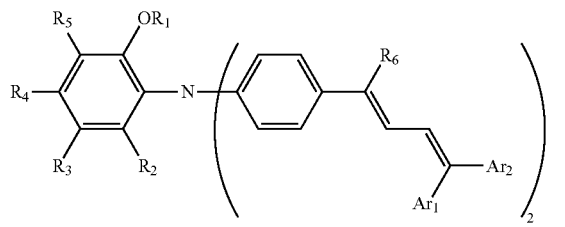

(1)

In General Formula (1), $OR_1$ represents an alkoxy group having 2 to 8 carbon atoms. $R_2$ to $R_6$ each independently represent a hydrogen atom or an alkyl group having 1 to 8 carbon atoms. $Ar_1$ and $Ar_2$ each independently represent a hydrogen atom, an aryl group having 6 to 20 carbon atoms and optionally substituted with an alkyl group having 1 to 6 carbon atoms, an aryl group having 6 to 20 carbon atoms and optionally substituted with an alkoxy group having 1 to 6 carbon atoms, a cycloalkyl group having 3 to 10 carbon atoms, or a 3- to 10-membered heterocyclic group. Note that the case where $Ar_1$ and $Ar_2$ are both a hydrogen atom is excluded.

A method for manufacturing a triphenylamine derivative according to the present disclosure is for manufacturing the triphenylamine derivative represented by General Formula (1) and involves a process of causing a reaction represented by Reaction Formula (1).

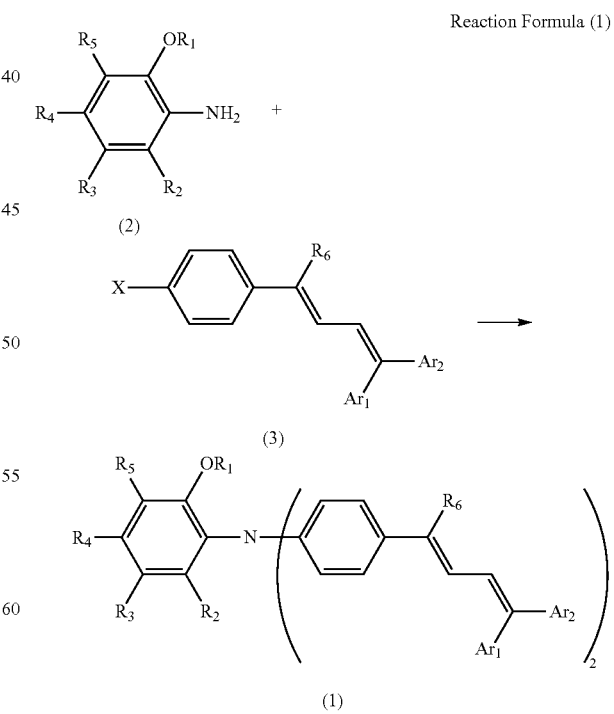

Reaction Formula (1)

In General Formulas (1) to (3) in Reaction Formula (1), X represents a halogen atom. $OR_1$ represents an alkoxy group having 2 to 8 carbon atoms. $R_2$ to $R_6$ each independently represent a hydrogen atom or an alkyl group having 1 to 8 carbon atoms. $Ar_1$ and $Ar_2$ each independently represent a hydrogen atom, an aryl group having 6 to 20 carbon atoms and optionally substituted with an alkyl group having 1 to 6 carbon atoms, an aryl group having 6 to 20 carbon atoms and optionally substituted with an alkoxy group having 1 to 6 carbon atoms, a cycloalkyl group having 3 to 10 carbon atoms, or a 3- to 10-membered heterocyclic group. Note that the case where $Ar_1$ and $Ar_2$ are both a hydrogen atom is excluded.

An electrophotographic photosensitive member according to the present disclosure contains the triphenylamine derivative represented by General Formula (1) described above.

DETAILED DESCRIPTION

First Embodiment

Triphenylamine Derivative

Figure 1A:
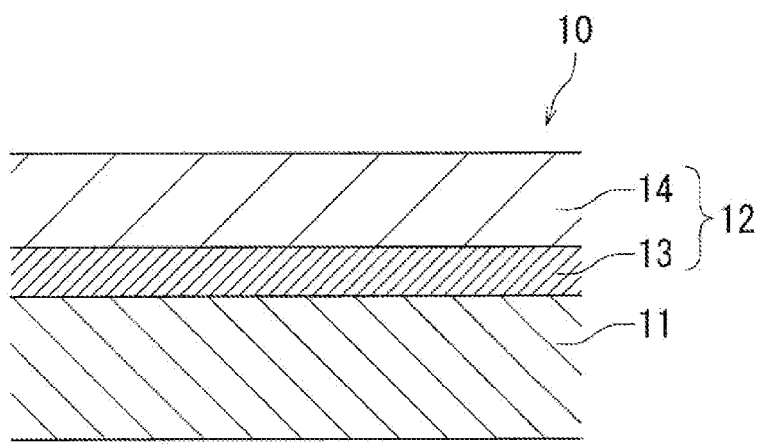
FIG. 1A is a schematic cross sectional view showing a structure of a multi-layered electrophotographic photosensitive member according to an embodiment of the present disclosure.

A first embodiment is directed to a triphenylamine derivative represented by General Formula (1). For example, the triphenylamine derivative is contained as the hole transport material in the photosensitive layer of an electrophotographic photosensitive member.

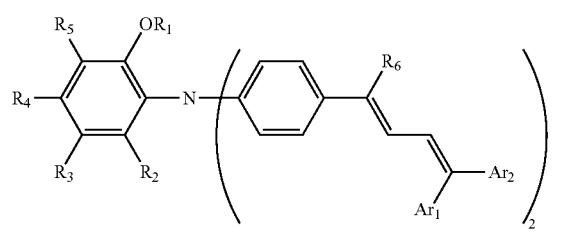

(1)

In General Formula (1), $OR_1$ represents an alkoxy group having 2 to 8 carbon atoms. $R_2$ to $R_6$ each independently represent a hydrogen atom or an alkyl group having 1 to 8 carbon atoms. $Ar_1$ and $Ar_2$ each independently represent a hydrogen atom, an aryl group having 6 to 20 carbon atoms and optionally substituted with an alkyl group having 1 to 6 carbon atoms, an aryl group having 6 to 20 carbon atoms and optionally substituted with an alkoxy group having 1 to 6 carbon atoms, a cycloalkyl group having 3 to 10 carbon atoms, or a 3- to 10-membered heterocyclic group. Note that the case where $Ar_1$ and $Ar_2$ are both a hydrogen atom is excluded.

According to the present disclosure, the triphenylamine derivative represented by General Formula (1) has, at the ortho position of an arylamine group not having butadienyl group, an alkoxy group having a predetermined number of carbon atoms. With the photosensitive layer containing a triphenylamine derivative having such a structure, the electrophotographic photosensitive member will have improved electrical characteristics. In particular, the residual potential is effectively suppressed and the crack resistance of the photosensitive layer surface improves.

The following is presumed to be the reason for that the use of the triphenylamine derivative represented by General Formula (1) ensures the electrophotographic photosensitive member to have excellent electrical characteristics and crack resistance.

The triphenylamine derivative represented by General Formula (1) has, at the ortho position of an arylamine group not having butadienyl group, an alkoxy group having a predetermined number of carbon atoms. This improves the solubility of the triphenylamine derivative in a solvent. As a result, the crystallization of the triphenylamine derivative is prevented at the time of forming the photosensitive layer and the uniform dispersion of the triphenylamine derivative in the photosensitive layer is ensured.

Because an alkoxy group having a predetermined number of carbon atoms is present at the ortho position of the arylamine group not having butadienyl group, the ionization potential of the triphenylamine derivative represented by General Formula (1) tends to be lower. This reduces the energy gap for charge transfer between the triphenylamine derivative represented by General Formula (1) and other components contained in the photosensitive layer (charge generating material, for example). As a result, the charge injection efficiency in the photosensitive layer improves effectively. In particular, multi-layer electrophotographic photosensitive members is provided with a multi-layer photosensitive layer that includes a charge generating layer and a charge transport layer. The triphenylamine derivative represented by General Formula (1) may be used as the hole transport material contained in the charge transport layer. This effectively improves the charge injection efficiency at the interface between the charge generating layer and the charge transport layer.

Further, when the photosensitive layer is formed as a coating layer, the use of the triphenylamine derivative represented by General Formula (1) ensures good compatibility with materials contained in the application liquid (such as solvent or resin). Still further, when the application liquid applied is later formed into a photosensitive layer, the use of the triphenylamine derivative represented by General Formula (1) together with various materials ensures to form the coating layer (photosensitive layer) to be dense and homogeneous. The photosensitive layers as above are less prone to erosion by chemical agents and to cracking (environmental stress cracking).

The application liquid applied may be formed into a photosensitive layer by thermal drying. In the process of thermal drying the application liquid into the photosensitive layer, thermal stress is caused due to the difference between the thermal expansion coefficients of the respective components contained in the application liquid. The thermal stress is one cause of reducing the homogeneity and density of the coating layer. However, the difference in the thermal expansion coefficients between the triphenylamine derivative represented by General Formula (1) and other components of the photosensitive layer is small. This is presumed to be the reason why the homogenous photosensitive layer having excellent crack resistance is formed.

As above, the triphenylamine derivative represented by General Formula (1) has, at the ortho position of an arylamine group not having butadienyl group, an alkoxy group having the predetermined carbon number. Therefore, the use of triphenylamine derivative in the photosensitive layer of an electrophotographic photosensitive member ensures necessary electrical characteristics and enhanced crack resistance.

To achieve the electron-donating ability to an extent sufficient to reduce the ionization potential, the alkoxy group in $OR_1$ preferably 2 to 4 carbon atoms.

In addition, in the triphenylamine derivative represented by General Formula (1), $R_2$ to $R_6$ are each independently represent a hydrogen atom or an alkyl group having 1 to 4 carbon atoms. More preferably, at least one of $R_2$ to $R_5$ is an alkyl group having 1 to 4 carbon atoms for the following reason. That is, a triphenylamine derivative having such a structure has a lipid solubility and a steric effect to the extent sufficient to improve the solubility in a solvent. Therefore, a photosensitive layer containing such a triphenylamine derivative is capable of maintaining sufficient mechanical characteristics.

More specifically, by introducing an appropriate number of alkyl groups having an appropriate chain length to the triphenylamine derivative represented by General Formula (1), the solubility of the triphenylamine derivative in a solvent improves along with the compatibility of the triphenylamine derivative with a resin. On the other hand, introducing an excessive number of long-chain substituents to the triphenylamine derivative represented by General Formula (1) is not desirable. The photosensitive layer containing such a triphenylamine derivative is inferior in mechanical characteristics needed as a coating layer.

Preferably, $R_2$ in the triphenylamine derivative represented by General Formula (1) is a hydrogen atom. When $R_2$ is a hydrogen atom, the molecular symmetry in the triphenylamine derivative represented by General Formula (1) is broken. This further improves the solubility of the triphenylamine derivative in a solvent.

Preferably, in addition, only either $Ar_1$ or $Ar_2$ in General Formula (1) is an aryl group having 6 to 20 carbon atoms and optionally substituted with an alkyl group having 1 to 6 carbon atoms, an aryl group having 6 to 20 carbon atoms and optionally substituted with an alkoxy group having 1 to 6 carbon atoms, a cycloalkyl group having 3 to 10 carbon atoms, or a 3- to 10-membered heterocyclic group, for the following reason. That is, when either $Ar_1$ or $Ar_2$ is the substituent or heterocyclic group described above, the spread of π electrons is controlled to a more appropriate state, which improves the charge transport efficiency.

Preferably, in addition, $R_6$ in General Formula (1) is a hydrogen atom for the following reason. That is, when $R_6$ is a hydrogen atom, the spread of π electrons is controlled to a more appropriate state, which improves the charge transport efficiency.

The following lists examples of substituents usable in the triphenylamine derivative according to the present disclosure.

Examples of the alkyl group usable as any of $R_2$ to $R_6$ include a methyl group, an ethyl group, a propyl group, an isopropyl group, an n-butyl group, a t-butyl group, a pentyl group, an isopentyl group, a neopentyl group, a hexyl group, a heptyl group, an n-octyl group, and an isooctyl group.

Examples of the alkoxy group usable as $OR_1$ include an ethoxy group, an n-propoxy group, an isopropoxy group, an n-butoxy group, an s-butoxy group, a t-butoxy group, a pentyloxy group, an isopentyloxy group, a neopentyloxy group, a hexyloxy group, a heptyloxy group, an n-octyloxy group, and an isooctyloxy group.

Examples of the functional group usable as $Ar_1$ or $Ar_2$ include the following.

Examples of the cycloalkyl group having 3 to 10 carbon atoms include cyclobutane, cycloheptane, and cyclohexane.

Examples of the 3- to 10-membered heterocyclic group include a furan ring, a thiophene ring, and a pyridine ring. Examples of the aryl group having 6 to 20 carbon atoms include a phenyl group, a tolyl group, a xylyl group, a mesityl group, a naphthyl group, an anthryl group, a phenanthryl group, and a cyclobutyl group.

Specific examples of the triphenylamine derivative according to the present disclosure include HTM-1 to HTM-4 respectively represented by Formulas (8) to (11) below.

HTM-1

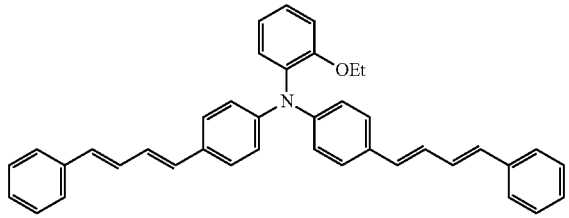

(8)

HTM-2

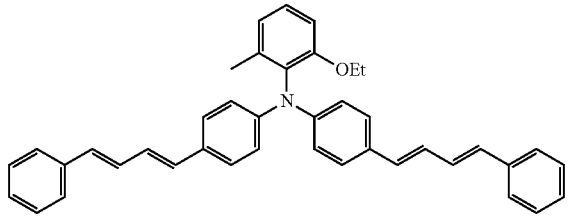

(9)

HTM-3

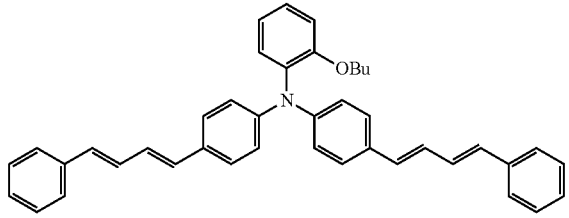

(10)

HTM-4

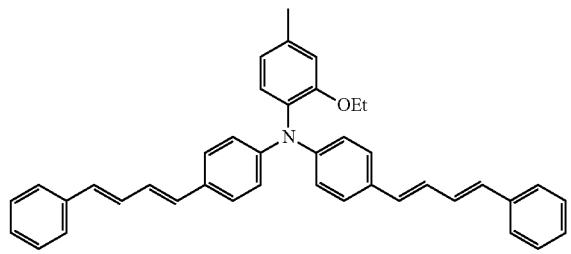

(11)

Second Embodiment

Method for Manufacturing Triphenylamine Derivative

A second embodiment of the present disclosure is directed to a method for manufacturing the triphenylamine derivative represented by General Formula (1). The manufacturing method according to the second embodiment involves a process of causing the reaction represented by Reaction Formula (1).

Reaction Formula (1)

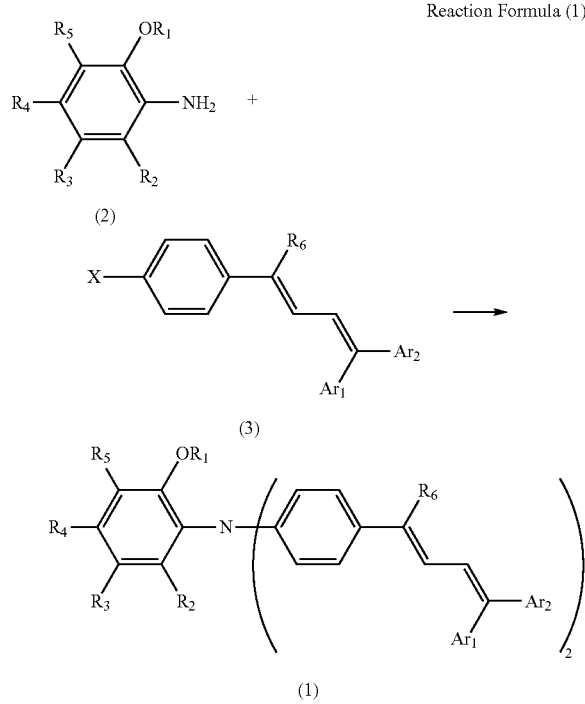

In General Formula (3) in Reaction Formula (1), X represents a halogen atom. In General Formulas (1) to (3), the substituents other than X are the same as those described relative to General Formula (1).

The following describes a method for manufacturing the triphenylamine derivative represented by General Formula (1). The manufacturing method includes a preparatory process and a synthesis process.

1. Preparatory Process (Synthesis of Halogenated Styryl Derivative Via Wittig Reaction)

In the preparatory process, a compound represented by General Formula (3) is prepared. The compound represented by General Formula (3) is the reactant in Reaction Formula (1). The substituents in General Formula (3) are the same as those in Reaction Formula (1).

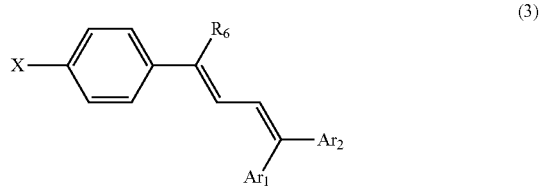

(3)

In the preparatory process, first, a reaction represented by Reaction Formula (2) below is caused. Through this, a compound represented by General Formula (12) reacts with triethyl phosphite to obtain phosphonate represented by General Formula (13).

Note that X' in General Formula (12) represents a halogen atom.

Reaction Formula (2)

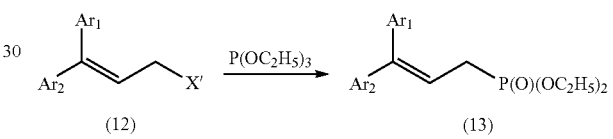

The reaction rate (mole ratio) of the compound represented by General Formula (12) to triethyl phosphite (=Compound Represented by General Formula (12):(Triethyl Phosphite) is preferably 1:1 to 1:2.5.

The above range of the reaction ratio of the compound represented by General Formula (12) to triethyl phosphite is preferred for the following reason. That is, when the ratio of triethyl phosphite added falls below the lower limit described above, the yield of the compound represented by General Formula (13) may be excessively reduced. On the other hand, when the ratio of the triethyl phosphite added exceeds the upper limit described above, the reaction represented by Reaction Formula (2) leaves an excessive amount of triethyl phosphite unreacted. This may render it difficult to purify phosphonate represented by General Formula (13).

The reaction represented by Reaction Formula (2) is preferably carried out at the reaction temperature within a range of 160° C. to 200° C. for the reaction time of 2 to 10 hours.

Next, the Wittig reaction represented by Reaction Formula (3) is caused. Through this, the resulting compound represented by General Formula (13) is caused to react with a compound represented by General Formula (14) to obtain the compound represented by General Formula (3). The Wittig reaction is caused in the presence of catalyst.

Reaction Formula (3)

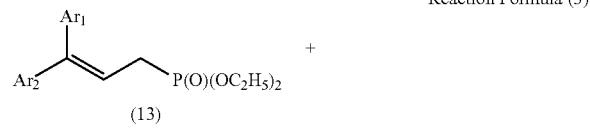

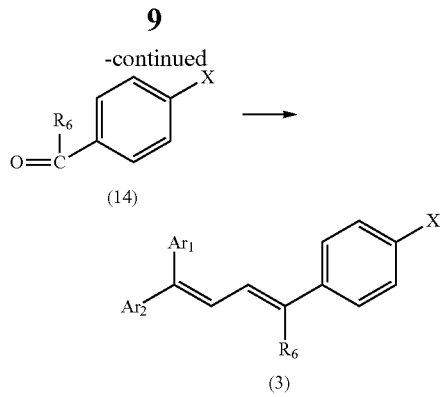

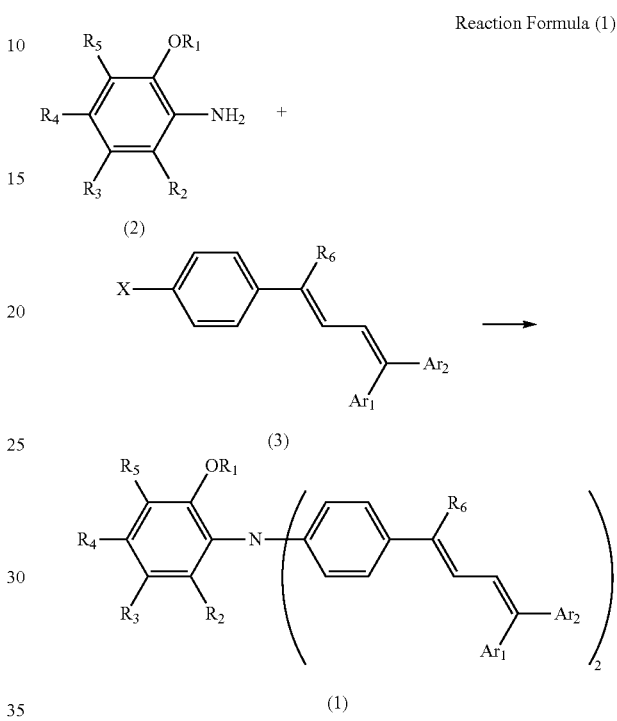

The reaction rate (mole ratio) of the compound represented by General Formula (13) to the compound represented by General Formula (14) (=Compound Represented by General Formula (13):Compound represented by General Formula (14)) is preferably 1:1 to 1:2.5.

The above-described reaction ratio of the compounds represented by General Formula (13) to the compounds represented by General Formula (14) is preferred for the following reason. That is, when the ratio of the added compound represented by General Formula (14) falls below the lower limit described above, the yield of the compound represented by General Formula (3) may be excessively reduced.

On the other hand, when the ratio of the added compound represented by General Formula (14) exceeds the upper limit described above, the reaction represented by Reaction Formula (3) leaves an excessive amount of the compound represented by General Formula (14) unreacted. This may render it difficult to purify the compound represented by General Formula (3).

The reaction represented by Reaction Formula (3) is preferably carried out at the reaction temperature within a range of −20° C. to 30° C. for the reaction time of 5 to 30 hours.

Examples of the catalyst used in the reaction represented by Reaction Formula (3) include sodium alkoxide (sodium methoxide or sodium ethoxide), metal hydride (sodium hydride or potassium hydride), and metal salt (n-butyl-lithium, for example). These catalysts may be used alone, or two or more of these catalysts may be used in combination.

In the reaction represented by Reaction Formula (3), the amount of the catalyst to be added is preferably one mole or more and two moles or less with respect to one mole of the compound represented by General Formula (14) for the following reason.

The above amount is preferred for the following reason. That is, when the amount of catalyst is less than one mole, a risk arises that the reactivity between the compounds represented by General Formulas (13) and (14) may be excessively reduced. On the other hand, when the amount of catalyst exceeds two moles, the control of the reaction between the compounds represented by General Formulas (13) and (14) is rendered difficult.

Note that the respective reactions represented by Reaction Formulas (2) and (3) are carried out in a solvent, for example. Examples of the solvent include ethers (diethyl ether, tetrahydrofuran, and dioxane), halogenized hydrocarbons (methylene chloride, chloroform, and dichloroethane), and aromatic hydrocarbons (benzene and toluene).

2. Synthesis of Triphenylamine Derivative

The following now describes the synthesizing process. In the synthesizing process, the compound represented by General Formula (3) prepared in the preparatory process is made to react with the compound represented by General Formula (2) that is separately prepared. This generates the triphenylamine derivative represented by General Formula (1), which is the end object. Note that Reaction Formula (1) represents a coupling reaction.

In General Formula (3) in Reaction Formula (1), X represents a halogen atom. In General Formulas (1) to (3), the substituents other than X are the same as those described relative to General Formula (1).

The reaction rate (mole ratio) of the compound represented by General Formula (3) to the compound represented by General Formula (2) (=Compound Represented by General Formula (3):Compound Represented by General Formula (2)) is preferably 5:1 to 1:1, more preferably 3:1 to 1:1, and even more preferably 2:1 to 1:1.

That is, when the ratio of the added compound represented by General Formula (3) falls below the lower limit described above, the yield of the triphenylamine derivative represented by General Formula (1) may be excessively reduced. On the other hand, when the ratio of the added compound represented by General Formula (3) exceeds the upper limit described above, an excessive amount of the compound represented by General Formula (3) is left unreacted. This may render it difficult to purify the triphenylamine derivative represented by General Formula (1).

The reaction represented by Reaction Formula (1) is preferably carried out at the reaction temperature within a range of 80° C. to 140° C. for the reaction time of 2 to 10 hours.

In addition, it is preferable to use a palladium catalyst in Reaction Formula (1).

The use of a palladium compound as the catalyst effectively lowers the activation energy for the reaction represented by Reaction Formula (1). Consequently, the yield of the triphenylamine derivative represented by General Formula (1) can be improved even more.

Examples of the palladium compound described above include quadrivalent palladium compounds (hexachloro palladium (IV) sodium tetrahydrate and hexachloro palladium (IV) potassium tetrahydrate), divalent palladium compounds (palladium chloride(II), palladium bromide(II), palladium acetate(II), palladium acetylacetate(II), dichlorobis(benzonitrile) palladium(II), dichlorobis(triphenylphosphine)palladium(II), dichlorotetramine palladium(II), and dichloro(cycloocta-1,5-diene)palladium(II)), and other palladium compounds (tris(dibenzylideneacetone)dipalladium(0), tris(dibenzylideneacetone)dipalladium(0) chloroform complex, and tetrakis(triphenylphosphine)palladium(0)). These catalysts may be used alone, or two or more of these catalysts may be used in combination.

The amount of the palladium compound to be added is preferably 0.0005 moles or more and 20 moles or less with respect to 1 mole of the compound represented by General Formula (2), and more preferably 0.001 moles or more and 1 mole or less.

In addition, the reaction represented by Reaction Formula (1) is preferably carried out in the presence of a base.

In the presence of a base, the reaction represented by Reaction Formula (1) immediately neutralizes the hydrogen halide which is generated in the reaction system to improve the catalytic activity. Consequently, the yield of the triphenylamine derivative represented by General Formula (1) can be improved.

The base mentioned above may be inorganic base or organic base. Although the organic base is not particularly limited, preferred examples of the organic base include alkali metal alkoxides (sodium methoxide, sodium ethoxide, potassium methoxide, potassium ethoxide, lithium tert-butoxide, sodium tert-butoxide, and potassium tert-butoxide) and sodium tert-butoxide is particularly preferred. In addition, examples of the inorganic base include tripotassium phosphate and caesium fluoride.

On condition that 0.005 moles of a palladium compound is added to one mole of the compound represented by General Formula (2), the amount of the palladium compound to be added is preferably 1 mole or more and 10 moles or less and more preferably 1 mole or more and 5 mole or less for the following reason.

Note that the reaction represented by Reaction Formula (1) is carried out in a solvent. Examples of the solvent include xylene, toluene, tetrahydrofuran, and dimethyl formamide.

Third Embodiment

A third embodiment of the present disclosure is directed to an electrophotographic photosensitive member. Typically, the electrophotographic photosensitive member according to the third embodiment includes a substrate and a photosensitive layer. The photosensitive layer is disposed on or above the substrate. The photosensitive layer may be either a multi- or a single-layer photosensitive layer. That is, the electrophotographic photosensitive member according to the third embodiment may be a multi- or a single-layer electrophotographic photosensitive member. The photosensitive layer (multi- or single-layer photosensitive layer) contains the triphenylamine derivative represented by General Formula (1).

The following describes a multi-layer electrophotographic photosensitive member 10 and a single-layer electrophotographic photosensitive member 20 with reference to FIGS. 1A-1C, and FIGS. 2A and 2B, focusing on the differences with the contents already described in the first and second embodiments.

Multi-Layer Electrophotographic Photosensitive Member

Figure 1B:
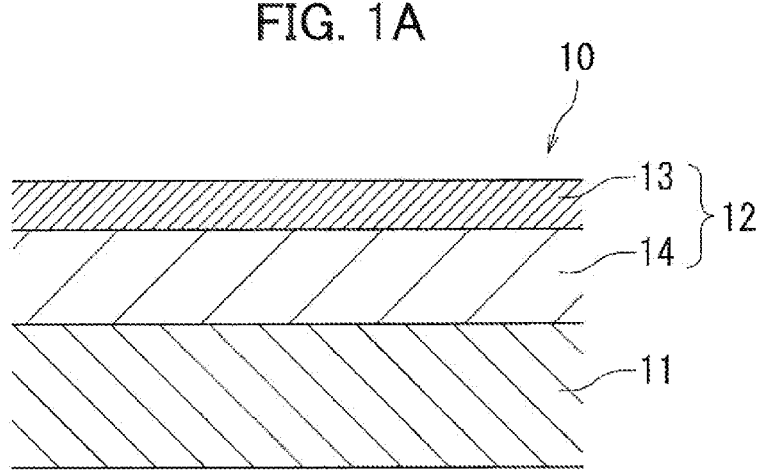
FIG. 1B is a schematic cross sectional view showing another structure of the multi-layered electrophotographic photosensitive member according to the embodiment of the present disclosure.
Figure 1C:
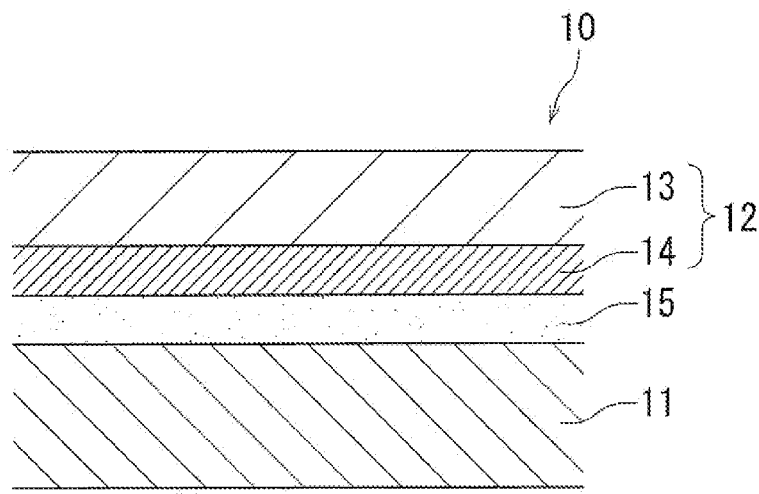
FIG. 1C is a schematic cross sectional view showing a yet another structure of the multi-layered electrophotographic photosensitive member according to the embodiment of the present disclosure.

FIGS. 1A to 1C are schematic cross sectional views each showing a structure of a multi-layered electrophotographic photosensitive member 10.

Basic Structure

As shown in FIG. 1A, the multi-layer electrophotographic photosensitive member 10 includes a substrate 11 and a multi-layer photosensitive layer 12. The multi-layer photosensitive layer 12 includes a charge transport layer 14 and a charge generating layer 13.

The multi-layer electrophotographic photosensitive member 10 is manufactured by stacking the charge generating layer 13 and the charge transport layer 14 on the substrate 11. The charge generating layer 13 contains the charge generating material. The charge transport layer 14 contains the charge transport material. The charge generating layer 13 and the charge transport layer 14 are stacked by, for example, applying an application liquid for a charge generating layer and an application liquid for a charge transport layer.

The multi-layer electrophotographic photosensitive member 10 may be structured such that the charge transport layer 14 is disposed on the substrate 11 and the charge generating layer 13 is disposed on the charge transport layer 14 as shown in FIG. 1B.

As for the multi-layer electrophotographic photosensitive member 10 shown in FIG. 1B, the charge transport layer 14 is typically thicker than the charge generating layer 13. Therefore, the charge transport layer 14 is more resistant to rupture than the charge generating layer 13. In view of this, the multi-layer electrophotographic photosensitive member 10 is preferably structured to include the charge transport layer 14 disposed on the charge generating layer 13 as shown in FIG. 1A.

It is also preferable to include an intermediate layer 15 (undercoat layer, for example) between the substrate 11 and the multi-layer photosensitive layer 12 as shown in FIG. 1C.

Typically, the hole transport material is the only charge transport material contained in the charge transport layer 14 used. However, the charge transport layer 14 may contain an electron transport material as well as the hole transport material both as the charge transport material.

Substrate

The substrate 11 may be made from various conductive materials. Examples of the substrate 11 include substrates made from a metal (iron, aluminum, copper, tin, platinum, silver, vanadium, molybdenum, chromium, cadmium, titanium, nickel, palladium, indium, stainless steel, or brass), substrates made from a plastic material deposited or laminated with any of the metals mentioned above, and glass substrates coated with a material such as aluminum iodide, anodized aluminum, tin oxide, or indium oxide.

It is sufficient that the substrate 11 itself or the surface of the substrate 11 is conductive. In addition, the substrate 11 preferably has a sufficient mechanical strength in use.

The shape of the substrate 11 can be appropriately selected depending on the structure of the image forming apparatus to which the substrate 11 is applied. For example, the substrate 11 may take the form of a sheet or a drum.

Intermediate Layer (Undercoat Layer)

The multi-layer electrophotographic photosensitive member 10 may include the intermediate layer 15 on the substrate 11, as shown in FIG. 1C. The intermediate layer 15 contains a predetermined resin.

The provision of the intermediate layer 15 in the multi-layer electrophotographic photosensitive member 10 can improve the adhesion of the substrate 11 and the multi-layer photosensitive layer 12. In addition, the intermediate layer 15 may contain a predetermined fine powder to scatter incident light and suppress occurrence of interference fringes. In addition, the intermediate layer 15 containing the predetermined fine powder suppresses the charge injection from the substrate 11 to the multi-layer photosensitive layer 12 during non-exposer to light. Note that the charge injection from the substrate 11 to the multi-layer photosensitive layer 12 causes fogging or black spots in images formed. The fine powder that may be contained in the intermediate layer 15 is not specifically limited may be any fine powder having light-scattering or light-dispersion characteristics. Examples of the fine powder include white pigments (titanium oxide, zinc oxide, hydrozincite, zinc sulfide, white lead, and lithopone), organic pigments as extender (alumina, calcium carbonate, and barium sulphate), fluororesin particles, benzoguanamine resin particles, and styrene resin particles.

The thickness of the intermediate layer 15 is preferably 0.1 µm or more and 50 µm or less.

Charge Generating Layer 13

The charge generating layer 13 contains the charge generating material. It is preferable to use at least one selected from the group consisting of a metal-free phthalocyanine (τ- or X-form), a titanyl phthalocyanine (α- or Y-form), hydroxygallium phthalocyanine (V-form), and chlorogallium phthalocyanine (II-form).

The content of the charge generating material is preferably 5 parts by mass or more and 1,000 parts by mass or less with respect to 100 parts by mass of the resin for the charge generating layer (base resin).

Examples of the base resin used in the charge generating layer 13 include polycarbonate reins (bisphenol A type, bisphenol Z type, and bisphenol C type), polyester resins, methacryl resins, acrylic resins, polyvinyl chloride resins, polystyrene resins, polyvinyl acetate resins, styrene-butadiene copolymer resins, vinylidene chloride-acrylonitrile copolymer resins, polyvinyl chloride-vinyl acetate-maleic anhydride resins, silicone resins, silicone-alkyd resins, phenol-formaldehyde resins, styrene-alkyd resins, and N-vinylcarbazole resins. These resins may be used alone, or two or more of these resins may be used in combination.

The thickness of the charge generating layer 13 is preferably 0.1 µm or more and 5 µm or less.

Charge Transport Layer

The charge transport layer 14 contains the hole transport material as the charge transport material. The hole transport material used is the above-described triphenylamine derivative represented by General Formula (1).

The above-described triphenylamine derivative represented by General Formula (1) is used as the hole transport material for the following reason. That is, as described in detail with respect to the first embodiment, with the use of the triphenylamine derivative represented by General Formula (1) as the hole transport material, excellent electrical characteristics and crack resistance are achieved.

The content of the triphenylamine derivative represented by General Formula (1) is preferably 30 parts by mass or more and 100 or less with respect to 100 parts by mass of the resin for the charge transport layer (binder resin).

When the content of the triphenylamine derivative represented by General Formula (1) falls within the range described above, the dispersibility of the triphenylamine derivative represented by General Formula (1) in the charge transport layer increases to achieve excellent electrical characteristics.

That is, when the content of the triphenylamine derivative represented by General Formula (1) is less than 30 parts by mass, the amount of the triphenylamine derivative may be too small to achieve sufficient sensitivity characteristics. On the other hand, when the content of the triphenylamine derivative represented by General Formula (1) exceeds 100 parts by mass, its dispersibility in the charge transport layer is reduced, which makes the triphenylamine derivative more prone to crystallization or to reduce the charge transport efficiency.

The content of the triphenylamine derivative represented by General Formula (1) is more preferably 35 parts by mass or more and 95 parts by mass or less with respect to 100 parts by mass of the binder resin contained in the charge transport layer, and even more preferably 40 parts by mass or more and 90 parts by mass or less.

The charge transport layer 14 may additionally contain a hole transport material other than the triphenylamine derivative represented by General Formula (1). Examples of such other hole transport materials include nitrogen containing cyclic compounds and condensed polycyclic compounds. Examples of the nitrogen containing cyclic compounds and condensed polycyclic compounds include triphenyl amine based compounds (excluding the triphenylamine derivative represented by General Formula (1)), oxadiazole based compounds, such as 2,5-di(4-methylaminophenyl)-1,3,4-oxadiazole, styryl based compounds, such as 9-(4-diethylaminostyryl)anthracene, carbazole based compounds, such as polyvinyl carbazole, organic polysilane compounds, pyrazoline based compounds, such as 1-phenyl-3-(p-dimethylaminophenyl)pyrazoline, hydrazone based compounds, indole based compounds, oxazole based compounds, isoxazole based compounds, thiazole based compounds, thiadiazole based compounds, imidazole base compounds, pyrazole based compounds, and triazole based compounds. These hole transport materials may be used alone, or two or more of these hole transport materials may be used in combination.

When a hole transport material other than the triphenylamine derivative represented by General Formula (1) is additionally contained, the content of the other hole transport material is preferably 1 part by mass or more and 100 parts by mass or less with respect to 100 parts by mass of the triphenylamine derivative represented by General Formula (1).

The charge transport layer 14 may contain the electron transport material as the charge transport material. Examples of the electron transport material include quinone derivatives, anthraquinone derivatives, malononitrile derivatives, thiopyran derivatives, trinitrothioxanthone derivatives, 3,4,5,7-tetranitro-9-fluorenone derivatives, dinitroanthracene derivatives, dinitroacridine derivatives, nitroanthraquinone derivatives, dinitroanthraquinone derivatives, tetracyanoethylene, 2,4,8-trinitrothioxanthone, dinitrobenzene, dinitroanthracene, dinitroacridine, nitroanthraquinone, dinitroanthraquinone, succinic anhydride, maleic anhydride, and dibromomaleic anhydride. These electron transport materials may be used alone, or two or more of these electron transport materials may be used in combination.

When the charge transport layer 14 contains the electron transport material, the content of the electron transport material is preferably 1 part by mass or more and 50 parts by mass or less with respect to 100 parts by mass of the triphenylamine derivative represented by General Formula (1).

Examples of the binder resin used in the charge transport layer 14 include thermoplastic resins (polycarbonate resins, polyester resins, and polyarylate resins as well styrene-butadiene copolymers, styrene-acrylonitrile copolymers, styrene-maleic acid copolymers, acrylic copolymers, styrene-acrylic acid copolymers, polyethylene, ethylene-vinyl acetate copolymers, chlorinated polyethylene, polyvinyl chloride, polypropylene, ionomer, vinyl chloride-vinyl acetate copolymers, alkyd resins, polyamide, polyurethane, polysulfone, diallyl phthalate resins, ketone resins, polyvinyl butyral resins, and polyether resins), thermosetting resins (silicone resins, epoxy resins, phenol resins, urea resins, and melamine resins), and photocurable resins (epoxy acrylate, and urethane-acrylate). These binder resins may be used alone or two or more of the binder resins may be used as a mixture or as a copolymer.

The thickness of the charge transport layer 14 is preferably 5 μm or more and 50 μm or less.

A method for manufacturing the multi-layer electrophotographic photosensitive member 10 includes the following processes, for example.

First, a solvent, the charge generating material, the base resin, and one or more additives as needed are mixed to prepare an application liquid for a charge generating layer (first application liquid). The application liquid thus prepared is applied on a substrate (aluminum element tube, for example) by dip coating, spray coating, bead coating, blade coating, roller coating, or the like, for example.

The applied liquid is then subjected to hot-air drying at 100° C. for 40 minutes, for example. As a result, the charge generating layer 13 having the predetermined thickness is formed.

The solvent used for the application liquid may be any of various organic solvents. Examples of the solvent include alcohols (methanol, ethanol, isopropanol, and butanol), aliphatic hydrocarbons (n-hexane, octane, and cyclohexane), aromatic hydrocarbons (benzene, toluene, and xylene), halogenated hydrocarbons (dichloromethane, dichloroethane, chloroform, carbon tetrachloride, and chlorobenzene), ethers (dimethyl ether, diethyl ether, tetrahydrofuran, ethylene glycol dimethyl ether, diethylene glycol dimethyl ether, 1,3-dioxolane, and 1,4-dioxolane), ketones (acetone, methyl ethyl ketone, and cyclohexane), esters (ethyl acetate, and methyl acetate), dimethyl formaldehyde, dimethyl formamide, and dimethyl sulfoxide. These solvents may be used alone or two or more of the solvents may be used in mixture.

Next, the triphenylamine derivative represented by General Formula (1), the binder resin, and one or more additives as needed are dispersed in a solvent to prepare an application liquid for a charge transport layer (second application liquid). The application liquid for a charge transport layer thus prepared is applied on the charge generating layer 13 formed in the preceding process, followed by drying.

The preparation and the application or drying of the application liquid may be carried out in the same manner as that of the charge generating layer 13.

Note that the electrophotographic photosensitive member according to the present disclosure is preferably the multi-layer electrophotographic photosensitive member 10 for the following reason.

That is, when the electrophotographic photosensitive member according to the present disclosure is the multi-layer electrophotographic photosensitive member 10, the triphenylamine derivative represented by General Formula (1) contained as the hole transport material effectively exhibits excellent electrical characteristic.

More specifically, when the electrophotographic photosensitive member according to the present disclosure is the multi-layer electrophotographic photosensitive member, the charge transfer needs to take place across the interface between the charge generating layer and the charge transport layer. The charge transport efficiency in such charge transfer may be limited. However, according to the third embodiment, the triphenylamine derivative represented by General Formula (1) is used as the hole transport material and therefore the ionization potential is ensured to be reduced. Consequently, the charges are stably transferred across the interface between the charge generating layer and the charge transport layer.

Single-Layer Electrophotographic Photosensitive Member

The electrophotographic photosensitive member according to the present disclosure may be the single-layer electrophotographic photosensitive member 20.

Figure 2A:
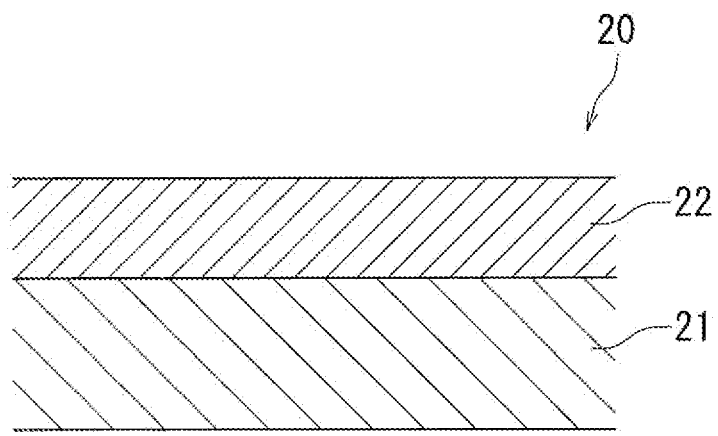
FIG. 2A is a schematic cross sectional view showing a structure of a single-layer electrophotographic photosensitive member according to an embodiment of the present disclosure.

As shown in FIG. 2A, the single-layer electrophotographic photosensitive member 20 includes a substrate 21 and a single-layer photosensitive layer 22, which is composed of a single layer. The single-layer photosensitive layer 22 is disposed on the substrate 21.

Figure 2B:
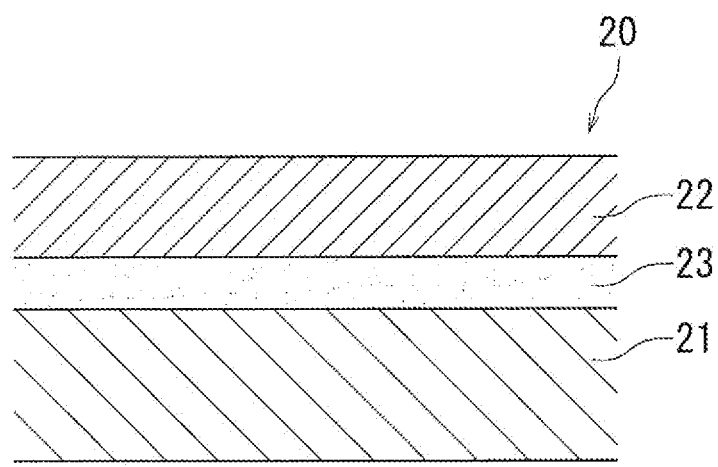
FIG. 2B is a schematic cross sectional view showing another structure of the single-layer electrophotographic photosensitive member according to the embodiment of the present disclosure.

The single-layer electrophotographic photosensitive member 20 may additionally include an intermediate layer (undercoat layer) 23 between the substrate 21 and the single-layer photosensitive layer 22 as shown in FIG. 2B, on condition that the characteristics of the photosensitive member are not adversely affected.

Any of the substrate and organic materials (such as the reins, charge transport material, and the electron transport material) of the single-layer electrophotographic photosensitive member 20 may be similar to the substrate and corresponding organic materials used in the multi-layer electrophotographic photosensitive member 10 described above.

The content of the triphenylamine derivative represented by General Formula (1) in the single-layer photosensitive layer 22 is preferably 20 parts by mass or more and 120 or less with respect to 100 parts by mass of the resin for the photosensitive layer (binder resin).

In addition, the single-layer photosensitive layer 22 of the single-layer electrophotographic photosensitive member 20 contains the hole transport material and the electron transport material. The content of the electron transport material is preferably 10 parts by mass or more and 70 parts by mass or less with respect to 100 parts by mass of the binder resin contained in the single-layer photosensitive layer 22.

The content of the charge generating material is preferably 0.2 parts by mass or more and 40 parts by mass or less with respect to 100 parts by mass of the binder resin contained in the single-layer photosensitive layer 22.

The thickness of the single-layer photosensitive layer 22 is preferably 5 μm or more and 100 μm or less.

EXAMPLES

The following describes the present disclosure in greater detail by way of examples. However, the present disclosure is not limited to these examples.

Example 1

2. Manufacture of Triphenylamine Derivative

Through a reaction represented by Reaction Formula (2-1) below, a compound represented by Formula (13-1) was generated.

More specifically, 15.2 g (100 mmol) of a compound represented by Formula (12-1) and 25 g (150.6024 mmol) of triethyl phosphite were put into a 200-ml flask, and the content of the flask was mixed at 180° C. for 8 hours to obtain a mixture.

Next, the thus obtained mixture was cooled to room temperature and the excess triethyl phosphite was distilled off under reduced pressure to obtain the compound (white liquid) represented by Formula (13-1) in an amount of 24.1 g (yield: 90%).

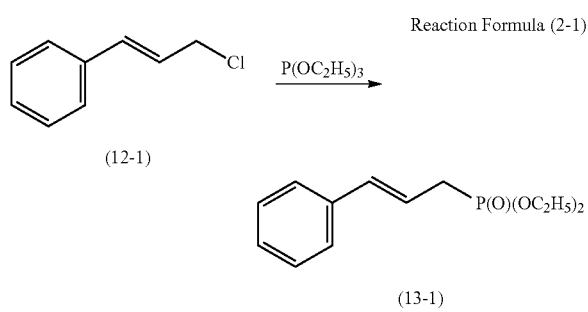

Reaction Formula (2-1)

Through a reaction represented by Reaction Formula (3-1) below, the compound represented by Formula (3-1) was generated.

More specifically, 13 g (50 mmol) of the compound represented by Formula (13-1) was put into a 500-ml two-necked flask, and argon gas purging was caused. After the argon gas purging, 100 ml of dried tetrahydrofuran (THF) and 9.3 g (50 mmol) of a methanol solution containing 28% by mass of sodium methoxide were added, followed by stirring at 0° C. for 30 minutes to obtain a reaction liquid.

Next, 7 g (50 mmol) of a compound represented by Formula (14-1) was added to and dissolved in 300 ml of the dried THF to obtain a dissolved matter. The dissolved matter was added to the stirred reaction liquid, followed by stirring at room temperature for 12 hours.

Then, the resulting reaction liquid was poured into ion exchanged water. Thereafter, toluene was poured to extract a compound represented by Formula (3-1). The organic phase (toluene phase) after the extraction was washed five times with ion exchanged water. The washed organic phase was dried over anhydrous sodium sulfate, followed by the filtration sodium sulfate. Then the organic phase was subjected to evaporation to dryness to obtain residue.

The thus obtained residue was recrystallized by using a mixture solvent of toluene and methanol (toluene/methanol=20 ml/100 ml) to obtain 10.22 g of white crystal of the compound represented by Formula (3-1) (yield: 85%).

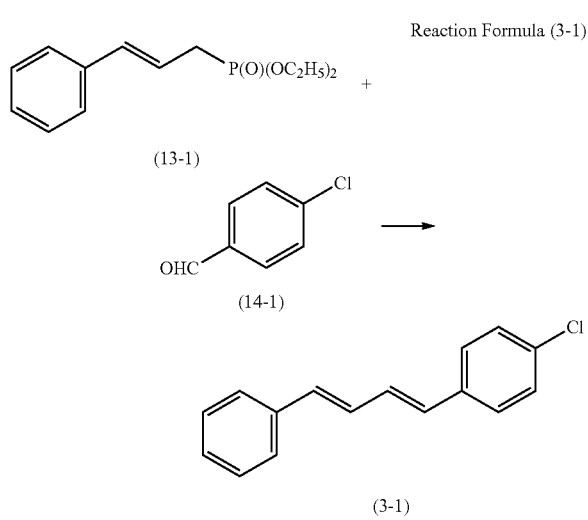

Reaction Formula (3-1)

Through the reaction represented by Reaction Formula (1-1) below, a triphenylamine derivative represented by Formula (8) (HTM-1) was obtained.

More specifically, 12 g (50 mmol) of the compound represented by Formula (2-1), 0.0662 g (0.189 mmol) of tricyclohexylphosphine (Pcy), 0.0864 g (0.0944 mmol) of tris(benzylideneacetone)dipalladium (Pd$_2$(dba)$_3$), 7.68 g (80 mmol) of sodium tert-butoxide (t-BuONa), and 3.425 g (25 mmol) of the compound represented by Formula (3-1) were put into a two-liter two-necked flask, followed by addition of 500 ml of distilled o-xylene. Thereafter, the content of the flask was subjected to argon gas purging, followed by stirring at 120° C. for 5 hours to allow for reaction.

Then, the reaction liquid was cooled to room temperature to obtain an organic phase. The organic phase was washed three times with ion exchanged water. The organic phase was then dried over anhydrous sodium sulfate and subjected to adsorption by using activated clay. Thereafter, o-xylene was distilled off under reduced pressure to obtain residue.

Figure 3:
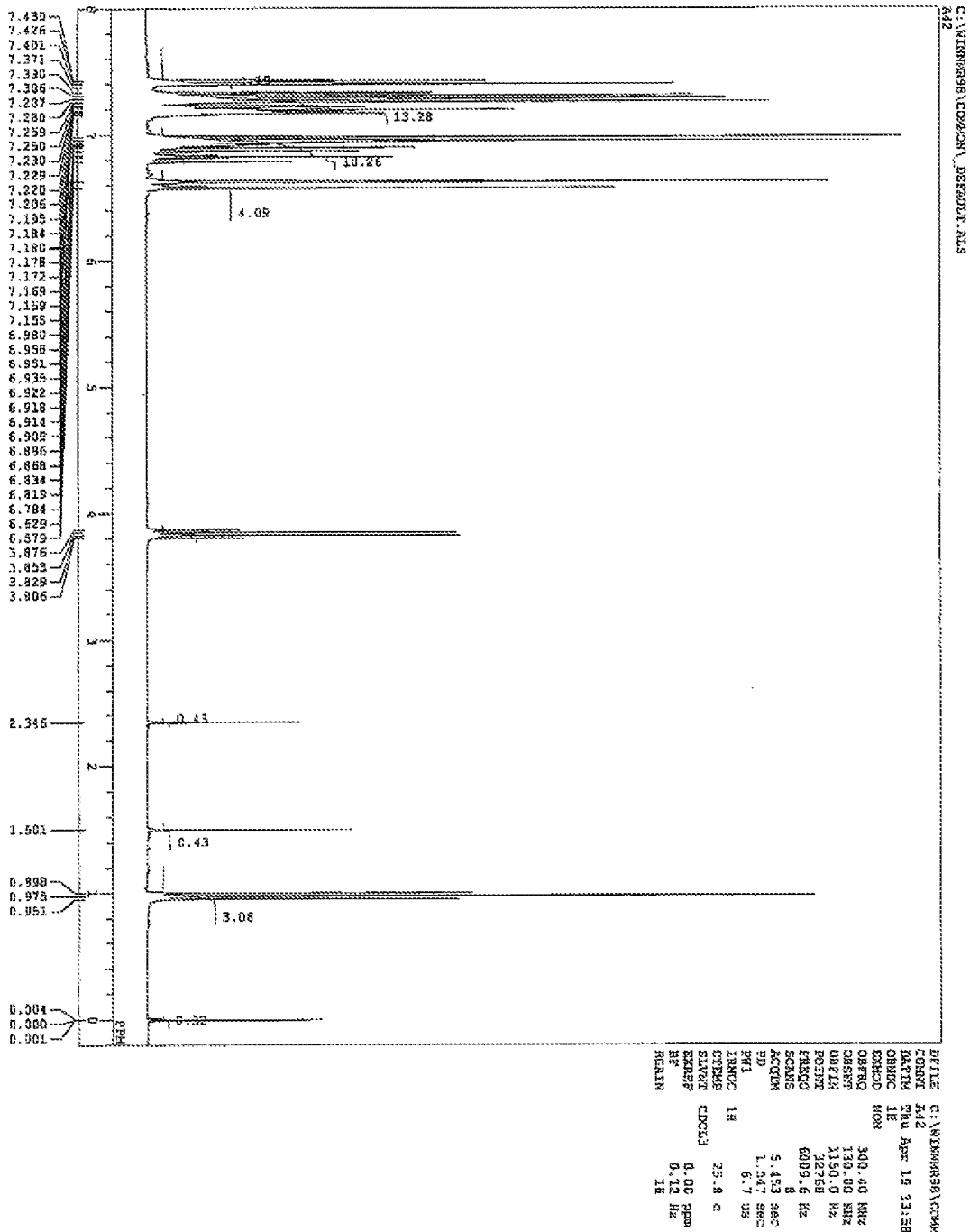
FIG. 3 is a $^1$H-NMR chart of a triphenylamine derivative HTM-1 obtained in Example 1 of the present disclosure.

The thus obtained residue was purified by using column chromatography (developing solvent: mixture of chloroform and hexane) to obtain the triphenylamine derivative HTM-1 (11.60 g) represented by Formula (8) (yield 85%). FIG. 3 shows a $^1$H-NMR chart of the triphenylamine derivative HTM-1 thus obtained.

The measurement on HTM-1 for the $^1$H-NMR chart was carried out at 300 MHz with the use of CDCl$_3$ as the solvent and trimethylsilyl (TMS) as the standard material.

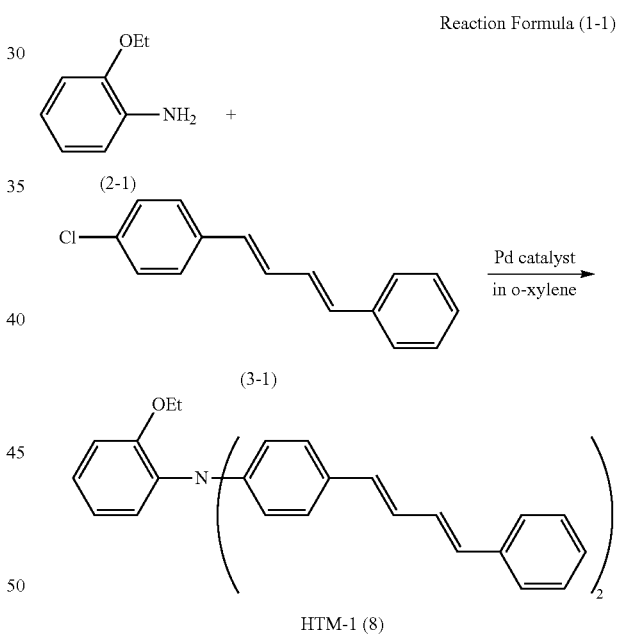

Reaction Formula (1-1)

Manufacture of Multi-Layer Electrophotographic Photosensitive Member Formation of Intermediate Layer First, titanium oxide having been subjected to a surface treatment (SMT-02 (trial product) manufactured by Tayca Corporation, number-average primary particle size: 10 nm) was prepared. More specifically, the titanium oxide having been subjected to a surface treatment with alumina and silica by using a bead mill, followed by a surface treatment with methyl hydrogen polysiloxane by wet dispersion was prepared. Then, 280 parts by mass of the titanium oxide and 100 parts by mass of a copolymerized polyamide resin (DIAMID X4685 manufactured by Daicel-Evonik.Ltd.) were mixed with 1,000 parts by mass of ethanol and 200 parts by mass of n-butanol both as a solvent. The materials were dispersed in the solvent for five hours and filtered with a filter (opening: 5 μm) to prepare an application liquid for an intermediate layer.

Next, the thus obtained application liquid for an intermediate layer was applied on an aluminum drum (substrate) measuring 30 mm in diameter and 238.5 mm in length. More specifically, the drum was immersed into the application liquid for an intermediate layer at the rate of 5 mm/sec with one end of the drum held upward. As a result, the application liquid for an intermediate layer was applied. Subsequently, the application liquid thus applied was cured through a heat treatment at 130° C. for 30 minutes to form an intermediate layer having a thickness of 1.5 μm.

Formation of Charge Generating Layer

Next, the first application liquid was prepared by mixing the following materials for two hours by using a bead mill to disperse the respective materials: 100 parts by mass of the Y-type crystal form titanyl phthalocyanine (CGM-1) as a charge generating material represented by Formula (15); 100 parts by mass of a polyvinyl butyral resin (Denka Butyral #6000EP manufactured by DENKI KAGAKU KOGYO KABUSHIKI KAISHA) as the base resin; and a mixture solvent of 4000 parts by mass of propylene glycol monomethyl ether and 4,000 parts by mass of tetrahydrofuran. The application liquid thus obtained was filtered with a filter (opening: 3 μm) and applied by dip coating on the surface of the intermediate layer formed in the above manner. The application liquid thus applied was dried at 50° C. for five minutes to form a charge generating layer having a thickness of 0.3 μm.

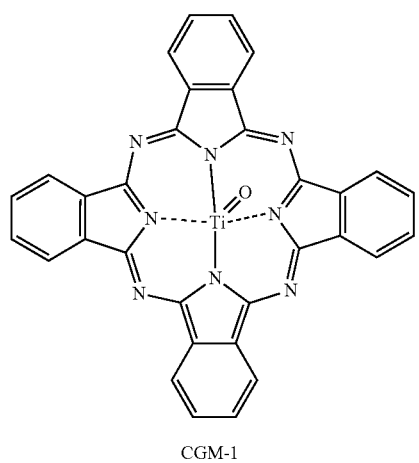

CGM-1

Formation of Charge Transport Layer

The second application liquid was prepared by adding the following materials into an ultrasonic disperser, followed by mixing for ten minutes to disperse the respective materials: 70 parts by mass of the triphenylamine derivative (HTM-1) represented by Formula (8) as the hole transport material, 5 parts by mass of BHT (di-tert-p-cresol)meta-terphenyl as an additive, 100 parts by mass of a Z polycarbonate resin (TS2050 manufactured by TEIJIN LIMITED, viscosity average molecular weight: 50,000) (Resin-1) represented by Formula (16) as the binder resin; and a mixture solvent of 430 parts by mass of tetrahydrofuran and 430 parts by mass of toluene both as a solvent.

The second application liquid thus obtained was applied on the surface of the charge generating layer formed in the above manner, in the same manner as the first application liquid.

Next, the application liquid thus applied was dried at 130° C. for 30 minutes to form a charge transport layer having a thickness of 20 μm. This completed a multi-layer electrophotographic photosensitive member of Example 1.

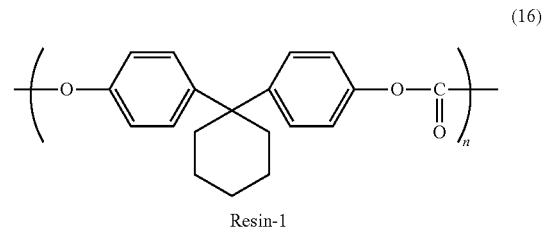

Resin-1

Example 2

In Example 2, a triphenylamine derivative (HTM-2) represented by Formula (9) was obtained through the reaction represented by Reaction Formula (1-1), by using a compound represented by Formula (2-2) instead of the compound represented by Formula (2-1).

Then, when a multi-layer electrophotographic photosensitive member was manufactured, the triphenylamine derivative (HTM-2) represented by Formula (9) was used as the hole transport material.

Other than the above, the triphenylamine derivative and the multi-layer electrophotographic photosensitive member were manufactured and evaluated through the same sequence as those for Example 1. The evaluation results are shown in Table 1 below.

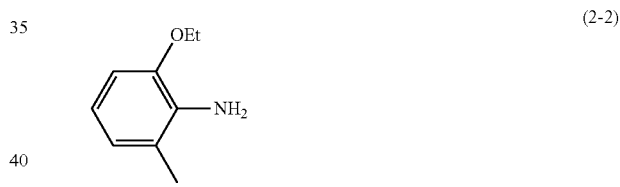

Example 3

In Example 3, a triphenylamine derivative (HTM-3) represented by Formula (10) was obtained through the reaction represented by Reaction Formula (1-1), by using a compound represented by Formula (2-3) instead of the compound represented by Formula (2-1).

Then, when a multi-layer electrophotographic photosensitive member was manufactured, the triphenylamine derivative (HTM-3) represented by Formula (10) was used as the hole transport material.

Other than the above, the triphenylamine derivative and the multi-layer electrophotographic photosensitive member were manufactured and evaluated through the same sequence as those for Example 1. The evaluation results are shown in Table 1 below.

Example 4

In Example 4, a triphenylamine derivative (HTM-4) represented by Formula (11) was obtained through the reaction represented by Reaction Formula (1-1), by using a compound represented by Formula (2-4) instead of the compound represented by Formula (2-1).

Then, when a multi-layer electrophotographic photosensitive member was manufactured, the triphenylamine derivative (HTM-4) represented by Formula (11) was used as the hole transport material.

Other than the above, the triphenylamine derivative and the multi-layer electrophotographic photosensitive member were manufactured and evaluated through the same sequence as those for Example 1. The evaluation results are shown in Table 1 below.

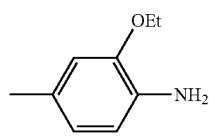

(2-4)

Comparative Example 1

In Comparative Example 1, a triphenylamine derivative (HTM-5) represented by Formula (6) was obtained through the reaction represented by Reaction Formula (1-1), by using a compound represented by Formula (2-5) instead of the compound represented by Formula (2-1).

Then, when a multi-layer electrophotographic photosensitive member was manufactured, the triphenylamine derivative (HTM-5) represented by Formula (6) was used as the hole transport material.

Other than the above, the triphenylamine derivative and the multi-layer electrophotographic photosensitive member were manufactured and evaluated through the same sequence as those for Example 1. The evaluation results are shown in Table 1 below.

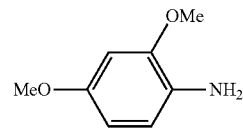

(2-5)

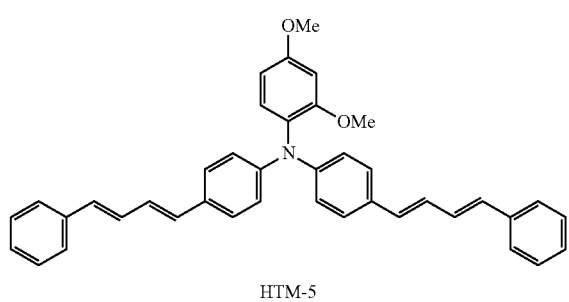

(6)

HTM-5

Comparative Example 2

In Comparative Example 2, a triphenylamine derivative (HTM-6) represented by Formula (7) was obtained through the reaction represented by Reaction Formula (1-1), by using a compound represented by Formula (2-6) instead of the compound represented by Formula (2-1).

Then, when a multi-layer electrophotographic photosensitive member was manufactured, the triphenylamine derivative (HTM-6) represented by Formula (7) was used as the hole transport material.

Other than the above, the triphenylamine derivative and the multi-layer electrophotographic photosensitive member were manufactured and evaluated through the same sequence as those for Example 1. The evaluation results are shown in Table 1 below.

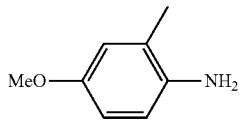

(2-6)

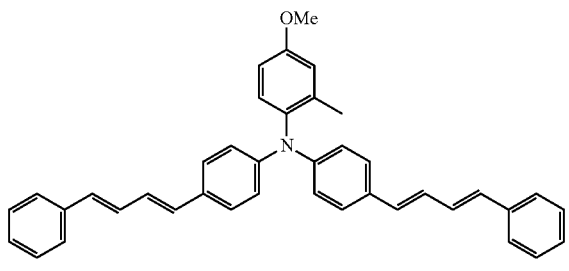

(7)

HTM-6

Comparative Example 3

In Comparative Example 3, a triphenylamine derivative (HTM-7) represented by Formula (17) was obtained through the reaction represented by Reaction Formula (1-1), by using a compound represented by Formula (2-7) instead of the compound represented by Formula (2-1).

Then, when a multi-layer electrophotographic photosensitive member was manufactured, the triphenylamine derivative (HTM-7) represented by Formula (17) was used as the hole transport material.

Other than the above, the triphenylamine derivative and the multi-layer electrophotographic photosensitive member were manufactured and evaluated through the same sequence as those for Example 1. The evaluation results are shown in Table 1 below.

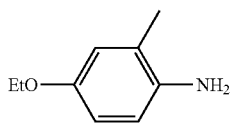

(2-7)

-continued (17)

HTM-7

Comparative Example 4

In Comparative Example 4, a triphenylamine derivative (HTM-8) represented by Formula (18) was obtained through the reaction represented by Reaction Formula (1-1), by using a compound represented by Formula (2-8) instead of the compound represented by Formula (2-1).

Then, when a multi-layer electrophotographic photosensitive member was manufactured the triphenylamine derivative (HTM-8) represented by Formula (18) was used as the hole transport material.

Other than the above, the triphenylamine derivative and the multi-layer electrophotographic photosensitive member were manufactured and evaluated through the same sequence as those for Example 1. The evaluation results are shown in Table 1 below.

(2-8)

PhO—⟨ ⟩—NH$_2$ (18)

HTM-8

Comparative Example 51

In Comparative Example 5, a triphenylamine derivative (HTM-9) represented by Formula (5) was obtained through the reaction represented by Reaction Formula (1-1), by using a compound represented by Formula (2-9) instead of the compound represented by Formula (2-1).

Then, when a multi-layer electrophotographic photosensitive member was 7•HTM-11•5.55•11.4•Very Good•–700•–92•Poor••Comparative used as the hole transport material.

Other than the above, the triphenylamine derivative and the multi-layer electrophotographic photosensitive member were manufactured and evaluated through the same sequence as those for Example 1. The evaluation results are shown in Table 1 below.

(2-9)

(5)

HTM-9

Comparative Example 6

In Comparative Example 6, a triphenylamine derivative (HTM-10) represented by Formula (19) was obtained through the reaction represented by Reaction Formula (1-1), by using a compound represented by Formula (2-10) instead of the compound represented by Formula (2-1).

Then, when a multi-layer electrophotographic photosensitive member was manufactured, the triphenylamine derivative (HTM-10) represented by Formula (19) was used as the hole transport material.

Other than the above, the triphenylamine derivative and the multi-layer electrophotographic photosensitive member were manufactured and evaluated through the same sequence as those for Example 1. The evaluation results are shown in Table 1 below.

(2-10)

n-Bu—⟨ ⟩—NH$_2$ (19)

HTM-10

Comparative Example 7

In Comparative Example 7, a triphenylamine derivative (HTM-11) represented by Formula (20) was obtained through the reaction represented by Reaction Formula (1-1), by using a compound represented by Formula (2-11) instead of the compound represented by Formula (2-1).

Then, when a multi-layer electrophotographic photosensitive member was manufactured, the triphenylamine derivative (HTM-11) represented by Formula (20) was used as the hole transport material.

Other than the above, the triphenylamine derivative and the multi-layer electrophotographic photosensitive member were manufactured and evaluated through the same sequence as those for Example 1. The evaluation results are shown in Table 1 below.

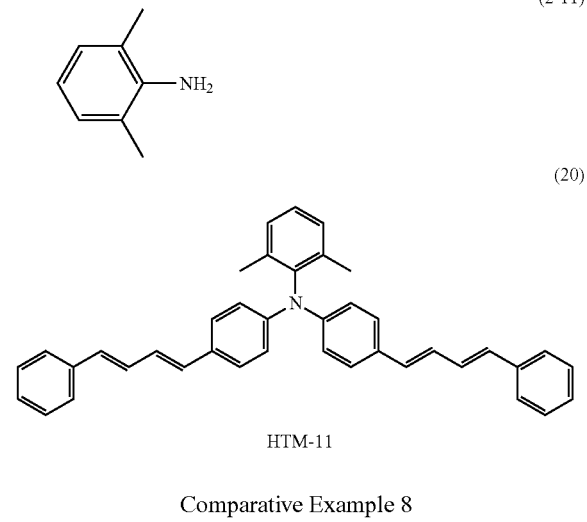

HTM-11

Comparative Example 8

In Comparative Example 8, a triphenylamine derivative (HTM-12) represented by Formula (4) was obtained through the reaction represented by Reaction Formula (1-1), by using a compound represented by Formula (2-12) instead of the compound represented by Formula (2-1).

Then, when a multi-layer electrophotographic photosensitive member was manufactured, the triphenylamine derivative (HTM-12) represented by Formula (4) was used as the hole transport material.

Other than the above, the triphenylamine derivative and the multi-layer electrophotographic photosensitive member were manufactured and evaluated through the same sequence as those for Example 1. The evaluation results are shown in Table 1 below.

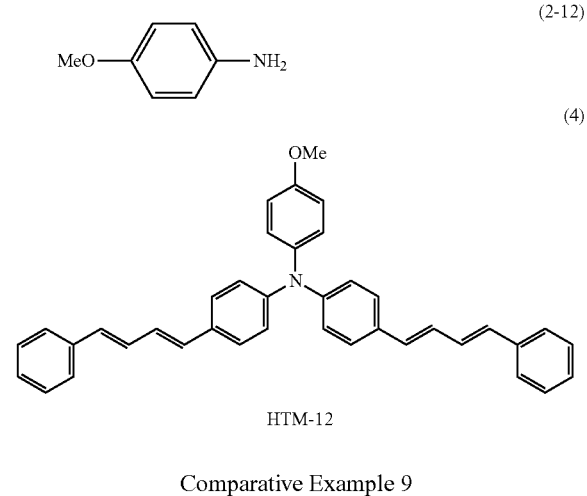

HTM-12

Comparative Example 9

In Comparative Example 9, a triphenylamine derivative (HTM-13) represented by Formula (21) was obtained through the reaction represented by Reaction Formula (1-1), by using a compound represented by Formula (2-13) instead of the compound represented by Formula (2-1).

Then, when a multi-layer electrophotographic photosensitive member was manufactured, the triphenylamine derivative (HTM-13) represented by Formula (21) was used as the hole transport material.

Other than the above, the triphenylamine derivative and the multi-layer electrophotographic photosensitive member were manufactured and evaluated through the same sequence as those for Example 1. The evaluation results are shown in Table 1 below.

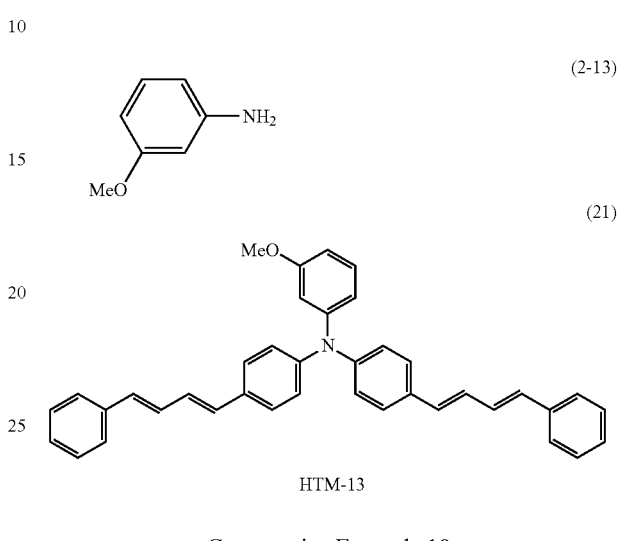

HTM-13

Comparative Example 10

In Comparative Example 10, a triphenylamine derivative (HTM-14) represented by Formula (22) was obtained through the reaction represented by Reaction Formula (1-1), by using a compound represented by Formula (2-14) instead of the compound represented by Formula (2-1).

Then, when a multi-layer electrophotographic photosensitive member was manufactured, the triphenylamine derivative (HTM-14) represented by Formula (22) was used as the hole transport material.

Other than the above, the triphenylamine derivative and the multi-layer electrophotographic photosensitive member were manufactured and evaluated through the same sequence as those for Example 1. The evaluation results are shown in Table 1 below.

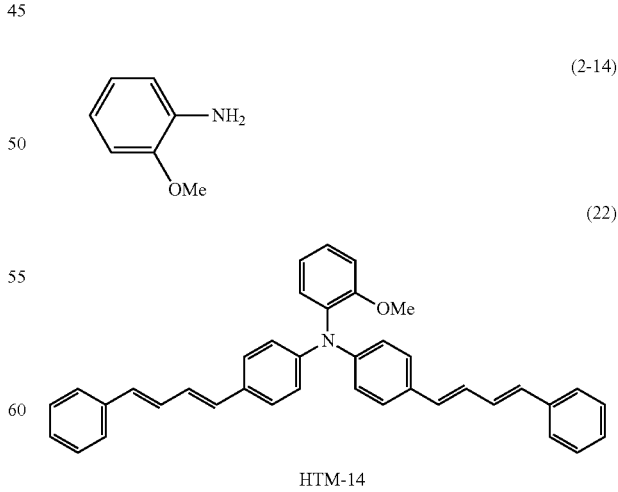

HTM-14

The respective triphenylamine derivatives and the respective multi-layer electrophotographic photosensitive members were evaluated in the following manner.

(1) Evaluations of Triphenylamine Derivatives
<Evaluation of Solubility>

The thus obtained triphenylamine derivatives HTM-1 to HTM-14 each as the hole transport material were evaluated for the solubility. A small amount of tetrahydrofuran was added to 100 mg of each triphenylamine derivative under the temperature of 25° C. Then, the resulting sample was vibrated and left to stand. This process was repeated to measure the added amount X (mg) of tetrahydrofuran dissolved in the triphenylamine derivative to saturation. With the added amount X, the equation below gives the solubility.

$$\text{Solubility (\%)} = \{100/(100+X)\} \times 100$$

<Evaluation of Ionization Potentials>

The respective triphenylamine derivatives HTM-1 to HTM-14 were each evaluated for the ionization potential. An atmosphere type ultraviolet photoelectron analyzing apparatus (AC-1 manufactured by Riken Keiki Co., Ltd.) was used to measure the ionization potential.

(2) Evaluation of Multi-Layer Electrophotographic Photosensitive Members
<Evaluation of Residual Potential>

The respective multi-layer electrophotographic photosensitive members of Examples 1 to 4 and Comparative Examples 1 to 10 were evaluated for the residual potential. First, a drum sensitivity test device manufactured by Gentec Inc. was used to charge the surface of each of the thus obtained photosensitive members to −700 V.

Then, the surface of the multi-layer electrophotographic photosensitive member was exposed to monochromatic light (wavelength: 780 nm, half-width: 20 nm, and light intensity: 0.4 µJ/cm$^2$) which was extracted from white light emitted by a halogen lamp with the use of a bandpass filter. The surface potential was measured after a lapse of 0.5 sec from the start of the irradiation and determined as the residual potential ($V_L$).

<Evaluation of Drum Appearance (Crystallization)>

The respective multi-layer electrophotographic photosensitive members of Examples 1 to 4 and Comparative Examples 1 to 10 were evaluated for the occurrence of crystallization on their surfaces. Under an optical microscope, the surface of each multi-layer electrophotographic photosensitive member was checked for any crystallization and evaluated according to the following criteria.

Very good: No crystallization was observed.
Good: Crystallization was observed in some portions.
Poor: Crystallization was observed in many portions.

<Evaluation of Crack Resistance>

The respective multi-layer electrophotographic photosensitive members of Examples 1 to 4 and Comparative Examples 1 to 10 were evaluated for the crack resistance. After oil (oleic triglyceride) was applied to ten locations on its surface, each multi-layer electrophotographic photosensitive member and left to stand for two days. Then, each surface was observed under an optical microscope to check occurrence of cracks and evaluated according to the following criteria.

Very good: No cracking occurred.
Good: Cracking occurred at one to three locations.
Poor: Cracking occurred at four or more locations.

Table 1 shows the evaluations of the triphenylamine derivatives and the multi-layer electrophotographic photosensitive members of Examples 1 to 4 and Comparative Examples 1 to 10.

TABLE 1

| | Hole Transport Material (Triphenylamine Derivative) | | | Evaluation of Multi-Layer Photosensitive Member | | | |
|---|---|---|---|---|---|---|---|
| | Type | Ionization Potential (eV) | THF Solubility (%) | Evaluation of Drum Appearance | Charged Potential $V_O$(V) | Residual Potential $V_L$(V) | Crack Resistance |
| Example 1 | HTM-1 | 5.38 | 25.0 | Very Good | −700 | −63 | Very Good |
| Example 2 | HTM-2 | 5.37 | 23.5 | Very Good | −700 | −65 | Very Good |
| Example 3 | HTM-3 | 5.39 | 24.1 | Very Good | −700 | −70 | Very Good |
| Example 4 | HTM-4 | 5.39 | 22.8 | Very Good | −700 | −75 | Very Good |
| Comparative Example 1 | HTM-5 | 5.33 | 20.0 | Very Good | −700 | −65 | Poor |
| Comparative Example 2 | HTM-6 | 5.38 | 24.5 | Very Good | −700 | −77 | Poor |
| Comparative Example 3 | HTM-7 | 5.39 | 25.8 | Very Good | −700 | −77 | Poor |
| Comparative Example 4 | HTM-8 | 5.48 | 21.0 | Very Good | −700 | −92 | Poor |
| Comparative Example 5 | HTM-9 | 5.46 | 12.3 | Very Good | −700 | −93 | Poor |
| Comparative Example 6 | HTM-10 | 5.42 | 17.8 | Very Good | −700 | −90 | Good |
| Comparative Example 7 | HTM-11 | 5.55 | 11.4 | Very Good | −700 | −92 | Poor |
| Comparative Example 8 | HTM-12 | 5.43 | 7.5 | Poor | Not measureable due to crystallization | | |
| Comparative Example 9 | HTM-13 | 5.45 | 6.1 | Poor | | | |
| Comparative Example 10 | HTM-14 | 5.43 | 6.3 | Poor | | | |

Manufacture of Single-Layer Electrophotographic Photosensitive Member

Example 51

The single-layer electrophotographic photosensitive member of Example 5 was manufactured in the following manner.

A mixture was obtained by adding and mixing the following materials in a vessel: 5 parts by mass of the X-type crystal form metal-free phthalocyanine (CGM-2) represented by Formula (23); 80 parts by mass of the hole transport material (HTM-1) represented by Formula (8); 50 parts by mass of the electron transport material (ETM-1) represented by Formula (24), 100 parts by mass of the polycarbonate resin represented by Formula (16) as the binder resin, 800 parts by mass of tetrahydrofuran as a solvent. Next, the resulting mixture was dispersed over 50 hours by using a ball mill to obtain an application liquid for a single-layer photosensitive layer (third application liquid).

Next, the thus obtained third application liquid was applied on an aluminum drum (substrate) measuring 30 mm in diameter and 238.5 mm in length. More specifically, the drum was immersed into the third application liquid at the rate of 5 mm/sec with one end of the drum held upward. As a result, the third application liquid was applied. The third application liquid thus applied was then cured through a heat treatment at 100° C. for 30 minutes to form a single-layer photosensitive layer having a thickness of 25 µm. As a result, the single-layer electrophotographic photosensitive member of Example 5 was obtained.

CGM-2

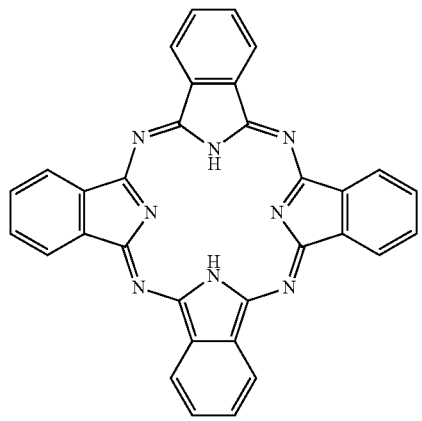

(23)

ETM-1

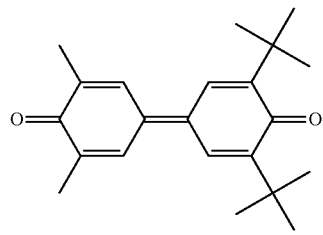

(24)

Example 6

The single-layer electrophotographic photosensitive member of Example 6 was manufactured and evaluated through the same sequence as those for Example 5, except for that the electron transport material used was a compound (ETM-2) represented by Formula (25) instead of ETM-1. The evaluation results are shown in Table 2 below.

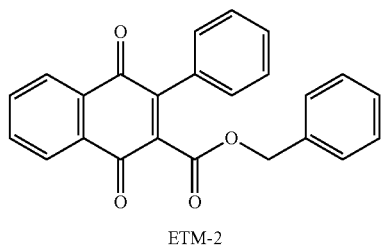

(25)

ETM-2

Example 7

The single-layer electrophotographic photosensitive member of Example 7 was manufactured and evaluated through the same sequence as those for Example 6, except for that the charge generating material used was the compound (CGM-1) represented by Formula (15) described above instead of CGM-2. The evaluation results are shown in Table 2 below.

Examples 8 to 10

The single-layer electrophotographic photosensitive members of Examples 8 to 10 were manufactured and evaluated respectively through the same sequence as those for Examples 5-7, except for that the holes transport material used was the compound (HTM-2) represented by Formula (10) described above instead of HTM-1. The evaluation results are shown in Table 2 below.

Comparative Examples 11 to 13

The single-layer electrophotographic photosensitive members of Comparative Examples 11 to 13 were manufactured and evaluated respectively through the same sequence as those for Examples 5-7, except for that the hole transport material used was the triphenylamine derivative (HTM-8) represented by Formula (18) described above instead of HTM-1. The evaluation results are shown in Table 2 below.

Comparative Examples 14 to 16

The single-layer electrophotographic photosensitive members of Comparative Examples 14 to 16 were manufactured and evaluated respectively through the same sequence as those for Examples 5-7, except for that the hole transport material used was the triphenylamine derivative (HTM-9) represented by Formula (5) described above instead of HTM-1. The evaluation results are shown in Table 2 below.

Comparative Examples 17 to 19

The single-layer electrophotographic photosensitive members of Comparative Examples 17 to 19 were manufactured and evaluated respectively through the same sequence as those for Examples 5-7, except for that the hole transport material used was the triphenylamine derivative (HTM-12) represented by Formula (4) described above instead of HTM-1. The evaluation results are shown in Table 2 below.

Evaluations of Single-Layer Electrophotographic Photosensitive Members

<Evaluation of Residual Potential>

The respective single-layer electrophotographic photosensitive members of Examples 5 to 10 and Comparative Examples 11 to 19 were evaluated for the residual potential after the following irradiation. First, the surface of each of single-layer photosensitive member was charged to about +700 V. Then, the residual potential on the surface of the photosensitive member was measured through the same sequence as in the measurement for Example 1, except for that the light intensity of monochromatic light used to irradiate the surface was 1.5 μJ/m².

<Evaluation of Drum Appearance (Crystallization)>

The respective single-layer electrophotographic photosensitive members of Examples 5 to 10 and Comparative Examples 11 to 19 were evaluated for the occurrence of crystallization on their surfaces. Similarly to the evaluations of drum appearance made for the multi-layer electrophotographic photosensitive members, the surface of each single-layer was observed under an optical microscope to check for any crystallization.

<Evaluation of Crack Resistance>

The respective single-layer electrophotographic photosensitive members of Examples 5 to 10 and Comparative Examples 11 to 19 were evaluated for the crack resistance. Similarly to the evaluations of crack resistance made for the multi-layer electrophotographic photosensitive members, after oil (oleic triglyceride) was applied to ten locations on its surface, each single-layer electrophotographic photosensitive member was left to stand for two days. Then, each surface was observed under an optical microscope to check and evaluate occurrence of cracks.

Table 2 shows the evaluations of the single-layer electrophotographic photosensitive members of Examples 5 to 10 and Comparative Examples 11 to 19. Evaluation of the physical properties of HTM-1, HTM-2, HTM-8, HTM-9 and HTM-12 are as shown in Table 1.

Example 11

The single-layer electrophotographic photosensitive member of Example 11 was manufactured in the following manner and evaluated for the occurrence of black spots. The single-layer electrophotographic photosensitive member of Example 11 was manufactured and evaluated through the same sequence as those for Example 5, except for that the electron transport material used was the compound (ETM-3) represented by Formula (26) instead of ETM-1. The evaluation results are shown in Table 3 below.

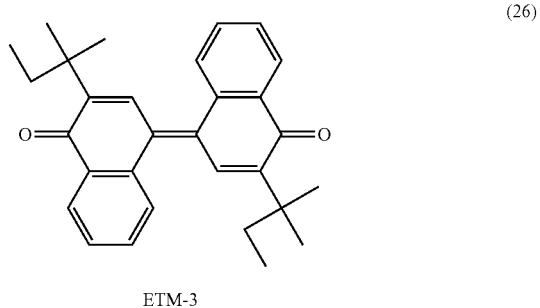 [SMILES: CCC(C)(C)C1=C/C(=C2/C=C(C(C)(C)CC)C(=O)c3ccccc32)c2ccccc2C1=O]

ETM-3

(26)

Example 12

The single-layer electrophotographic photosensitive member of Example 12 was manufactured and evaluated through the same sequence as those for Example 11, except for that the charge generating material used was the Y-type crystal form

TABLE 2

| | Components in Single-Layer Photosensitive Layer | | | Evaluation of Single-Layer Photosensitive Member | | | |
|---|---|---|---|---|---|---|---|
| | CGM | HTM | ETM | Charged Potential $V_O(V)$ | Residual Potential $V_L(V)$ | Evaluation of Drum Appearance | Crack Resistance |
| Example 5 | CGM-2 | HTM-1 | ETM-1 | 698 | 113 | Very Good | Very Good |
| Example 6 | CGM-2 | HTM-1 | ETM-2 | 700 | 116 | Very Good | Very Good |
| Example 7 | CGM-1 | HTM-1 | ETM-2 | 700 | 109 | Very Good | Very Good |
| Example 8 | CGM-2 | HTM-2 | ETM-1 | 700 | 116 | Very Good | Very Good |
| Example 9 | CGM-2 | HTM-2 | ETM-2 | 699 | 118 | Very Good | Very Good |
| Example 10 | CGM-1 | HTM-2 | ETM-2 | 699 | 112 | Very Good | Very Good |
| Comparative Example 11 | CGM-2 | HTM-8 | ETM-1 | 700 | 111 | Good | Poor |
| Comparative Example 12 | CGM-2 | HTM-8 | ETM-2 | 701 | 115 | Good | Poor |
| Comparative Example 13 | CGM-1 | HTM-8 | ETM-2 | 701 | 106 | Good | Poor |
| Comparative Example 14 | CGM-2 | HTM-9 | ETM-1 | 700 | 138 | Good | Poor |
| Comparative Example 15 | CGM-2 | HTM-9 | ETM-2 | 698 | 143 | Good | Poor |
| Comparative Example 16 | CGM-1 | HTM-9 | ETM-2 | 701 | 134 | Good | Poor |
| Comparative Example 17 | CGM-2 | HTM-12 | ETM-1 | Not measureable due to crystallization | | Poor | Poor |
| Comparative Example 18 | CGM-2 | HTM-12 | ETM-2 | | | Poor | Poor |
| Comparative Example 19 | CGM-1 | HTM-12 | ETM-2 | | | Poor | Poor | titanyl phthalocyanine (CGM-1) represented by Formula (15). The evaluation results are shown in Table 3 below.

Examples 13 and 14

The single-layer electrophotographic photosensitive members of Examples 13 and 14 were manufactured and evaluated respectively through the same sequence as those for Examples 11 and 12, except for that the hole transport material used was the triphenylamine derivative (HTM-2) represented by Formula (9). The evaluation results are shown in Table 3 below.

Comparative Examples 20 and 21

The single-layer electrophotographic photosensitive members of Comparative Examples 20 and 21 were manufactured and evaluated respectively through the same sequence as those for Examples 11 and 12, except for that the hole transport material used was the triphenylamine derivative (HTM-9) represented by Formula (5). The evaluation results are shown in Table 3 below.

Comparative Examples 22 and 23

The single-layer electrophotographic photosensitive members of Comparative Examples 22 and 23 were manufactured and evaluated respectively through the same sequence as those for Examples 11 and 12, except for that the hole transport material used was the triphenylamine derivative (HTM-12) represented by Formula (4). The evaluation results are shown in Table 3 below.

<Evaluation of Occurrence of Black Spots>

The respective single-layer electrophotographic photosensitive members of Examples 11 and 14 and Comparative Examples 20 to 23 were evaluated for the occurrence of black spots.

More specifically, each single-layer electrophotographic photosensitive member was mounted in a printer (DP-560 manufactured by KYOCERA Document Solutions Inc.) and a total of 5,000 prints were continuously produced on A4-size paper (high-quality copy paper manufactured by Fuji Xerox Co., Ltd.) under the environmental conditions of 40° C. and 90 RH %. The printer was then left to stand for 6 hours before producing a print of a blank original on A4-size paper. The number of black spots in the A4-size paper were counted and evaluated according to the following criteria.

Good: The number of black spots per A4-size sheet was less than 50.

Poor: The number of black spots per A4-size sheet was 50 or more.

Note that the number of black spots occurred serves as an index indicating the dispersibility or crystallizability of the triphenylamine derivative contained in the photosensitive layer.

When the triphenylamine derivative contained in the photosensitive layer becomes less dispersed or becomes crystalized, the triphenylamine derivative tends to aggregate excessively. Consequently, when the photosensitive member is charged, leakage current is likely to be caused at locations where the triphenylamine derivative aggregates. This tends to result in occurrence of black spots in an image formed.

Table 3 shows the evaluations of the single-layer electrophotographic photosensitive members of Examples 11 to 14 and Comparative Examples 20 to 23. Evaluation of the physical properties of HTM-1, HTM-2, HTM-9 and HTM-12 are as shown in Table 1.

TABLE 3

| | Components in Single-Layer Photosensitive Layer | | | Number of | Evaluation of Occurrence of |
|---|---|---|---|---|---|
| | CGM | HTM | ETM | Black Spots | Black Spots |
| Example 11 | CGM-2 | HTM-1 | ETM-3 | 36 | Very Good |
| Example 12 | CGM-1 | HTM-1 | ETM-3 | 40 | Very Good |
| Example 13 | CGM-2 | HTM-2 | ETM-3 | 48 | Very Good |
| Example 14 | CGM-1 | HTM-2 | ETM-3 | 44 | Very Good |
| Comparative Example 20 | CGM-2 | HTM-9 | ETM-3 | 72 | Poor |
| Comparative Example 21 | CGM-1 | HTM-9 | ETM-3 | 75 | Poor |
| Comparative Example 22 | CGM-2 | HTM-12 | ETM-3 | Not measureable due to crystallization | Poor |
| Comparative Example 23 | CGM-1 | HTM-12 | ETM-3 | | Poor |

As is apparent from Tables 1, 2, and 3, the triphenylamine derivative provided by the present disclosure has, at the ortho position of an arylamine group not having butadienyl group, an alkoxy group having a predetermined number of carbon atoms. Such triphenylamine derivative has an improved solubility in a solvent, an improved compatibility with a resin, and a lower ionization potential. With the use of such a triphenylamine derivative as the hole transport material, an electrophotographic photosensitive member having excellent electrical characteristics and excellent crack resistance can be provided.

What is claimed is:

1. A triphenylamine derivative comprising formula (1),

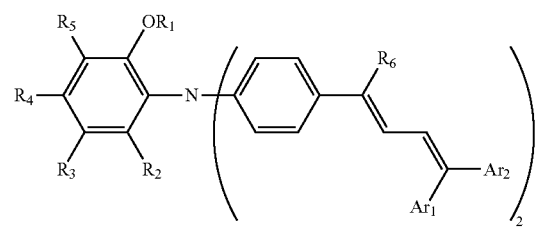

(1)

in formula (1),
$OR_1$ represents an alkoxy group having 2 to 4 carbon atoms,
$R_2$ to $R_6$ each independently represent a hydrogen atom or an alkyl group having 1 to 8 carbon atoms,
$Ar_1$ and $Ar_2$ each independently represent a hydrogen atom, an aryl group having 6 to 20 carbon atoms and optionally substituted with an alkyl group having 1 to 6 carbon atoms, an aryl group having 6 to 20 carbon atoms and optionally substituted with an alkoxy group having 1 to 6 carbon atoms, a cycloalkyl group having 3 to 10 carbon atoms, or a 3- to 10-membered heterocyclic group, and
where $Ar_1$ and $Ar_2$ are both a hydrogen atom is excluded.

2. A triphenylamine derivative according to claim 1, wherein
in formula (1), $R_2$ to $R_6$ each independently represent a hydrogen atom or an alkyl group having 1 to 4 carbon atoms.

3. A triphenylamine derivative according to claim 1, wherein
in formula (1), $R_2$ represents a hydrogen atom.

4. A triphenylamine derivative according to claim 1, wherein
in formula (1), $R_6$ represents a hydrogen atom.

5. A triphenylamine derivative according to claim 1 comprising any one of formulas (8), (9), (10), and (11), 6. An electrophotographic photosensitive member comprising:
a triphenylamine derivative according to claim 1.

7. A method for manufacturing a triphenylamine derivative according to claim 1, comprising:
causing a reaction represented by reaction formula (1),

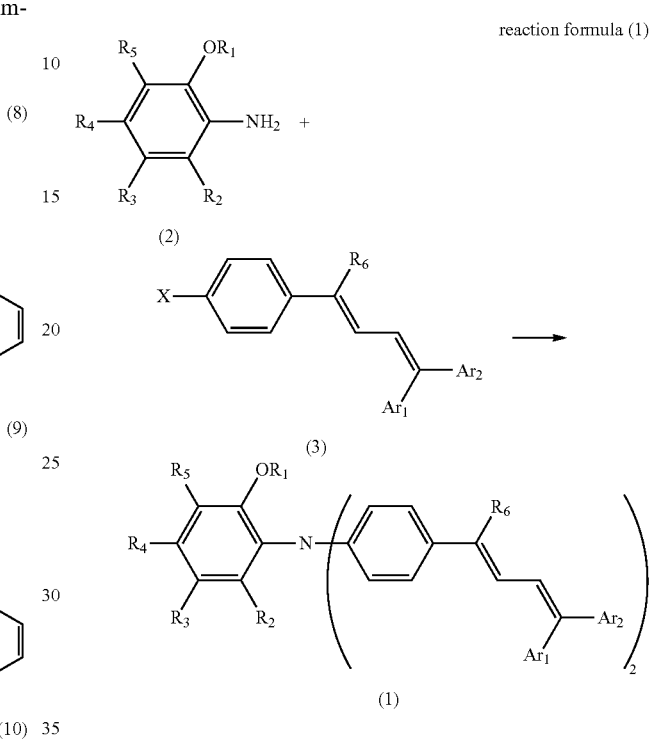

reaction formula (1)

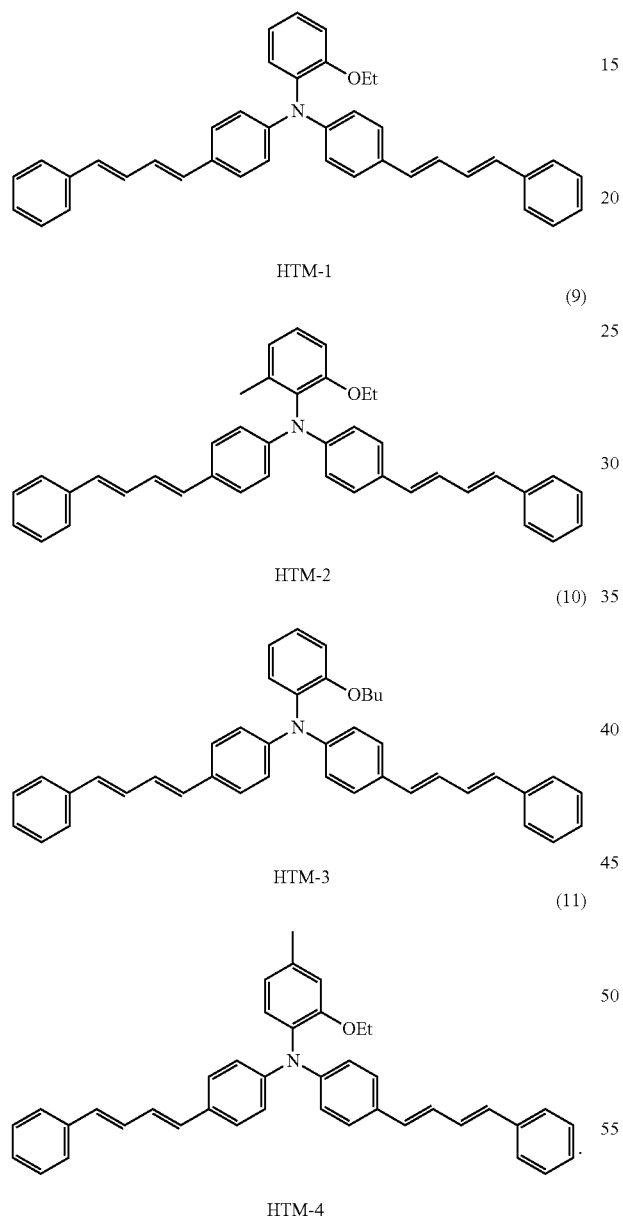

in each of formulas (1) to (3) in reaction formula (1),
X represents a halogen atom,
$OR_1$ represents an alkoxy group having 2 to 4 carbon atoms,
$R_2$ to $R_6$ each independently represent a hydrogen atom or an alkyl group having 1 to 8 carbon atoms,
$Ar_1$ and $Ar_2$ each independently represent a hydrogen atom, an aryl group having 6 to 20 carbon atoms and optionally substituted with an alkyl group having 1 to 6 carbon atoms, an aryl group having 6 to 20 carbon atoms and optionally substituted with an alkoxy group having 1 to 6 carbon atoms, a cycloalkyl group having 3 to 10 carbon atoms, or a 3- to 10-membered heterocyclic group, and
where $Ar_1$ and $Ar_2$ are both a hydrogen atom is excluded.

8. A method for manufacturing a triphenylamine derivative according to claim 7, wherein
a palladium compound is used as a catalyst in the reaction represented by reaction formula (1).

9. A method for manufacturing a triphenylamine derivative according to claim 7, wherein
the reaction represented by reaction formula (1) is carried out in the presence of a base.

* * * * *